(12) United States Patent
Cahoon et al.

(10) Patent No.: US 6,855,868 B2
(45) Date of Patent: Feb. 15, 2005

(54) GERANYLGERANYL PYROPHOSPHATE SYNTHASES

(75) Inventors: Rebecca E. Cahoon, Wilmington, DE (US); Mark E. Williams, Newark, DE (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 289 days.

(21) Appl. No.: 10/108,915

(22) Filed: Mar. 28, 2002

(65) Prior Publication Data

US 2002/0177204 A1 Nov. 28, 2002

Related U.S. Application Data

(62) Division of application No. 09/452,238, filed on Dec. 1, 1999, now Pat. No. 6,410,827.
(60) Provisional application No. 60/110,592, filed on Dec. 2, 1998.

(51) Int. Cl.$^7$ .......................... A01H 1/00; C07H 21/04; C07K 14/415; C12N 5/14; C12N 9/00
(52) U.S. Cl. ........................ 800/295; 435/6; 435/69.1; 435/468; 435/419; 435/252.3; 435/320.1; 530/370; 536/23.6; 800/278
(58) Field of Search .......................... 435/6, 69.1, 468, 435/419, 252.3, 320.1; 530/370; 536/23.6; 800/278, 295

(56) References Cited

PUBLICATIONS

Kuntz, "Identification of a cDNA for the plastid–located geranylgeranyl pyrophosphate synthase from Capsicum annuum: correlative increase in enzyme activity and transcript level during fruit ripening," *Plant J.*, 1992 Jan.;2(1):25–34.

Lai et al. "Guemao, a Drosophila bristle locus, encodes geranylgeranyl pyrophosphate Synthase," *Genetics*, 1998 Jun.; 149(2):1051–81.

Zhu et al., "Geranylgeranyl pyropphosphate synthase encoded by the newly isolated gene GGPS6 from Arabidopsis thallana is localized in mitochondria," *Plant Mol Biol.*, 1997 Oct.;35(3):331–41.

Adams et al., "Complementary DNA sequencing: expressed sequence tags and human genome project," *Science*, Jun. 21, 1991;252(5013):1651–6.

NCBI General Identifier No. 558925, geranylgeranyl pyrophosphate Synthase gi|558925|gb|AAA86688.1|[558925].

Aitken et al. "A cDNA encoding geranylgeranyl pyrophosphate synthase from white lupin," *Plant Physiol*, 1995 Jun.;108(2):837–8.

NCBI General Identifier No. 2464899 geranylgeranyl pyrophosphate synthase [Arabidopsis thaliana] gi|2464899 |amb|CAB16803.1|[2464899].

NCBI General Idenitifier No. 462174 sp|P34802|GGPP_ARATH[462174].

Scolnik et al., "Nucleotide sequence of an Arabidopsis cDNA for geranylgeranyl pyrophosphate synthase," *Plant Physiol.*, 1994 Apr;104(4):1469–70.

NCBI General Identifier No. 1419758 geranylgeranyl pyrophosphate synthase [Sinapis alba] gl|1419758|emb|CAA 67330.1|[1419758].

Bonk et al., "Chloroplast import of four carotenoid biosynthetic enzymes in vitro reveals differential fates prior to membrane binding and oligomeric assembly," *Eur J Biochem*, 1997 247;942–950.

NCBI General Identifier No. 5042458 putative geranylgeranyl pyrophosphate synthase [Oryza sativa (laponica cultivar–group)] gi|5042458|gb|AAD38295.1|AC007789_21 [5042458].

NCBI General Identifier No. 1063276 geranylgeranyl pyrophosphate synthase [*Catharanthus roseus*] gi|1063276|emb| CAA63486.1|[1063276].

Bantignies et al., "Nucleotide sequences of a *Catharanthus roseus* geranylgeranyl pyrophosphate synthase gene," *Plant Physiol*, 1996, vol. 110, p. 336.

NCBI General Identifier No. 735880 geranylgeranyl pyrophosphate synthase–related protein gi|735880|gb|AAA 81879.1|[735880].

Scolnick et al., "Nucleotide sequence of lycopene cyclase (GenBank L40176) from *Arabidopsis* (PGR95–019)m" *Plant Physiol.*, 1995, vol. 108, No. 3, p. 1343.

NCBI General Identifier No. 4467133 geranylgeranyl pyrophosphate synthase–related protein [Arabidopsis thellana] gi|4467133|emb|CAB37502.1|[4467133].

Bartley et al., "A tomato gene expressed during fruit ripening encodes an enzyme of the carotenoid biosynthesis pathway," *J Biol Chem.*, Mar. 16, 1992;267(8):5036–9.

Bork, "Powers and pitfalls in sequence analysis: the 70% hurdle," *Genome Res.* 2000 Apr;10(4):398–400.

*Primary Examiner*—Phuong T. Bui
(74) *Attorney, Agent, or Firm*—Lori Y. Beardell, Esq.; Gwilym J. O. Attwell, Esq.

(57) ABSTRACT

This invention relates to an isolated nucleic acid fragment encoding a geranylgeranyl pyrophosphate synthase. The invention also relates to the construction of a chimeric gene encoding all or a portion of the geranylgeranyl pyrophosphate synthase, in sense or antisense orientation, wherein expression of the chimeric gene results in production of altered levels of the geranylgeranyl pyrophosphate synthase in a transformed host cell.

13 Claims, 4 Drawing Sheets

Application No.: 10/108,915
7560*83 (BB1286USDIV)
Preliminary Amendment
Replacement Sheet

FIGURE 1A

```
              ***  *  ***  *****      *               *        **          *                         *
SEQ ID NO:18  MSSLNLGTWPRPTSMLNTPSHLLPP------FHTLT-LTTTLPKLASGTPKLISSFPLV
SEQ ID NO:22  MSALNLNAWPRP-------RSRSRSRSPTFHAVNKLPF----FTVTKRR---AFSL-
SEQ ID NO:26  MSAVNLNTWPRPSFILNQTATRRSRSSPTSHFFHGVNKLPSPISSLTVAKR----SFTL-
SEQ ID NO:45  M----------------LTKEDTVKD---------------------------------
              1                                                           60

***  ***                             *  **  *  ***        ***    ******
SEQ ID NO:18  SAVPTKEHTVTTQEIQLQDTPLNFDFKGYMIAKAHTVNQALDAAIALRDPHKIHQAMRYS
SEQ ID NO:22  SAVLT---VETEE----KPPIFDFKNYMLSKASAVNKGLDDSVSLREPKKIHEAMRYS
SEQ ID NO:26  SAVLTKEDTVETEE----KPPIFDFKNYMVSKASAVNKALDDAVSLREPQKIHEAMRYS
SEQ ID NO:45  -----KEEEEEEE-----KPR-FNFNLYMVEKSRSVNQALNDAVSLREPHKIHEAMRYS
              61                                                         120

***********  ******   *****  *  ***  *****     *********************
SEQ ID NO:18  LLAGGKRVRPVLCIAACELVGGTEATAI PAACAVEMIHTMSLIHDDLPCMDNDDLRRGKP
SEQ ID NO:22  LLAGGKRVRPVLCVAACELVGGHEATAMPAACALEMIHTMSLIHDDLPCMDNDDLRRGKP
SEQ ID NO:26  LLAGGKRVRPVLCVAACELVGGEEATAMPAACAIEMIHTMSLIHDDLPCMDNDDLRRGKP
SEQ ID NO:45  LLAGGKRVRPVLCIAACEVVGGNESTAMAAACSIEMIHTMSLIHDDLPCMDNDDLRRGKP
              121                                                        180

*** *  ***     *******  ****        *                *********
SEQ ID NO:18  TNHKVYGEDVAVLAGDALLAFAFEHVAASTEGVSPSRVVRAIGELAKSIGTEGLVAGQVV
SEQ ID NO:22  TNHTVFGEDVAVLAGDALLAFAFEHIAASTRGASAPRILRAIGELARSIGSEGLVAGQVV
SEQ ID NO:26  TNHKVFGEDVAVLAGDALLAFAFEHIAASTRGASPGRIVRAIGELARSIGSEGLVAGQVV
SEQ ID NO:45  TNHKVFGENIAVLAGDALLAFAFEHIAVSTSGVSPERIIGAIGELAKSIGTEGLVAGQVV
              181                                                        240
```

FIGURE 1B

```
                      ** ***         ** ******  * ******** *******       ******** *** *** *** **
SEQ ID NO:18          DIDSEGVANVGLETLEFIHVHKTAALLEAAVVLLGAIVGGGSDEEVEKLRKFARCIGLLFQ
SEQ ID NO:22          DINSEGLADVGLERLEFIHVHKTAALLEAVVLGAILGGGTDDEVEKLRKFARYIGLLFQ
SEQ ID NO:26          DINSEGLADVDLERLEFIHVHKTAALLEGAVVLGAILGGGTDDEVEKLRKFARYIGLLFQ
SEQ ID NO:45          DINSEGLCDIGLEKLEFIHLHKTAALLEGSVVVVGAILGGGCNEEVEKLRMFARYIGLMFQ
                      241                                                       300

****  ********  ** ******** *****************   ** *    **  ** ******
SEQ ID NO:18          VVDDILDVTKSSEELGKTAGKDLVADKVTYPKLLGIDKSKEFAQELLKDAKEQLSGFDPP
SEQ ID NO:22          VVDDILDVTKSSQELGKTAGKDLVADKVTYPKLLGIEKSKEFAAKLNKDAQDLAGFDPV
SEQ ID NO:26          VVDDILDVTKSSQELGKTAGKDLVADKVTYPKLLGIEKSKVFAAKLNKDAQDLVGFDPV
SEQ ID NO:45          VVDDVLDVTKSSKELGKTAGKDLVADKVTYPKLLGIEKSNEFAQKLNRDAQEQLSGFDPV
                      301                                                       360

*   *** *** ******
SEQ ID NO:18          KAAPLFALTNYIAYRQN
SEQ ID NO:22          KAAPLIALANYIAYRQN
SEQ ID NO:26          KAAPLIALANYIAYRQN
SEQ ID NO:45          KVAPLIALANYIAYSPN
                      361                377
```

FIGURE 1B

Application No.: 10/108,915
7560*83 (BB1286USDIV)
Preliminary Amendment
Replacement Sheet

FIGURE 2A

```
                    *                    *          ***       **         *
SEQ ID NO:34   M------ALS-SF--SMSLPFAKLPSTSKSTRFLPIRASSAAAAASPSFDLRLYWTSLIA
SEQ ID NO:38   MAPFAFATLPSSHICRLP-KPTNLKFRVRCSTAASSPSSVSTRSKAAGFDLKTYWANLMV
SEQ ID NO:44   M------ALS-SLFVSLPLPIPKPPSTSKSSRFLPIRASAAATASPSFDLRRYWTSLIS
SEQ ID NO:46   ML-FSGSAIPLSSFCSLPEKPHTLPMKL---SPAAIRSSSSSAPGSLNFDLRTYWTTLIT
               1                                                           60

**  *     ***         ***  *        ****            ***   *
SEQ ID NO:34   DVEAELDAAMPIRTPERIHSAMRYAVLPGAGNEGTAKRAPPVLCVAACELLGAPREAALP
SEQ ID NO:38   QINQKLDEAIPVQFPPQIYEAMRYSVLAKG----AKRAPPVMCISACELFGGSRLAAFP
SEQ ID NO:44   EVEGELDAAMPIRPPESIHNAMRHAVLPGAGKEGAAKRAPPVLCVAACELLGAPRAAALP
SEQ ID NO:46   EINQKLDEAIPVKHPAGIYEAMRYSVLAQG----AKRAPPVMCVAACELFGGDRLAAFP
               61                                                         120

** * ****** *   ****   * ********  *     *******  **  *
SEQ ID NO:34   AAVALEMLHAASLVHDDLPCFDAAPTRRGRPSTHAAYGTDMAVLAGDALFPLAYTHVIAH
SEQ ID NO:38   TACALEMVHAASLIHDDLPCMDDSPSRRGQPSNHTIYGVDMAILAGDALFPLGFRHIVSQ
SEQ ID NO:44   TAAALEMLHAASLVHDDLPCFDAAPTRRGRPSTHAAYGTDMAVLAGDALFPLAYTHVISR
SEQ ID NO:46   TACALEMVHAASLIHDDLPCMDDDPVRRGKPSNHTVYGSGMAILAGDALFPLAFQHIVSH
               121                                                        180

** *   *****  *         **  ** ******    *              ****
SEQ ID NO:34   TPSPDPVPHAVLLRVLGELARAVGSTGMAAGQFLDLAGATALGEAEVMKVLIKKFGEMAE
SEQ ID NO:38   TP-SDLVPESHLLRVIAEIARSVGSTGMAAGQFLDLEG----GPNAVGFIQEKKFGEMGE
SEQ ID NO:44   TPSPDPVSHAVLLRVLAELARTVGSTGMAAGQFLDLAGASALGEAEVMQVLIKKFGEMAE
SEQ ID NO:46   TP-PDLVPRATILRLITEIARTVGSTGMAAGQYVDLEG----GPFPLSFVQEKKFGAMGE
               181                                                        240
```

FIGURE 2B

```
                 ** **        * ***   **   **     *******   *    **  *       ***
SEQ ID NO:34     CSAACGAMLGGAGPDEEAALRRYGRTIGVLYQLVDDIRSAS----GNGKMRSNASVLRAL
SEQ ID NO:38     SSAVCGGFLAGAEDDEIERLRRYGRAVGVLYAVVDDIEERLKVEGDGDRKNKGKSYAEV
SEQ ID NO:44     CSAACGAMLGGAGPDEEAALRRYGRTIGVLYELVDDMRSAS----GNGKMRSNASVLRSL
SEQ ID NO:46     CSAVCGGLLGGATEDELQSLRRYGRAVGMLYQVVDDITED--------KKKSYDG-
                                                                          300
241

*             ***          **       *****  ******        ****
SEQ ID NO:34     -GMDRAL-GIVEELKAQAKMEADRFGDKYG--ERVLPLYSFVDYAVERGFELQDAATTP-
SEQ ID NO:38     YGVEKAI-EKAEELRAKAKEELDGFEKH--GERVFPLYSFVDYAFDRSFSVDDA---SG
SEQ ID NO:44     -GMDRAL-GIVEELKAQAKTEADRFGDKYG--DRVLPLYSFVDYAVERGFELQDAATAKL
SEQ ID NO:46     -GAEKGMMEMAEELKEKAKKELQVFDNKYGGGDTLVPLYTFVDYAAHRHFLL------PL
                                                                                360
301
```

GERANYLGERANYL PYROPHOSPHATE SYNTHASES

This application is a divisional application of U.S. application Ser. No 09/452,238, filed Dec. 1, 1199, issued on Jun. 25, 2002 as U.S. Pat. No. 410,827, which claims the benefit of U.S. Provisional Application No. 60/110,582, filed Dec. 2, 1998.

FIELD OF THE INVENTION

This invention is in the field of plant molecular biology. More specifically, this invention pertains to nucleic acid fragments encoding geranylgeranyl pyrophosphate synthase or geranylgeranyl pyrophosphate synthase-related protein in plants and seeds.

BACKGROUND OF THE INVENTION

Geranylgeranyl pyrophosphate (GGPP) synthase, also known as geranylgeranyl-diphosphate synthase, farnesyl transferase and geranylgeranyl synthetase is a key enzyme in plant terpenoid biosynthesis. The final product, GGPP, is the key precursor of several holoterpenoids such as carotenoids and meroterpenoids. One fate of GGPP is conversion to phytoene by phytoene synthase, the first committed step in carotenoid biosynthesis. Although not specific to carotenoid biosynthesis, GGPP synthase may be important in determining the total catorenoid content of a specific tissue. Expression of the GGPP synthase gene is strongly induced during the chloroplast to chromoplast transition which occurs in ripening peppers which have a high carotenoid content (Kuntz, M., et al. (1992) *Plant J*. 2:25–34).

GGPP also serves as precursor in the formation of defense-related substances like the phytoalexin casbene in castor bean and the diterpene phorbol which acts as a toxin against herbivores. GGPP is also a precursor of the important phytohormone gibberellin which regulates a variety of physiological processes that include initiation of seed germination, stimulation of stem elongation, stimulation of flowering/bolting and regulation of leaf/fruit senescence.

In animal systems, the importance of the enzyme GGPP synthase is demonstrated by the lethality of nonsense mutations in the locus that encodes the enzyme in *Drosophila* (Lai et al. (1998) *Genetics* 149:1051–1061). In plant systems, GGPP serves as precursor to many important metabolites that the enzyme responsible for its synthesis, GGPP synthase, appears to be an attractive target for herbicide discovery and design.

At least 6 different GGPP synthases have been identified in *Arabidopsis thaliana*. Beside differences in the amino acid sequence of the proteins and the nucleotide sequence of their genes, GGPP synthases accumulate in different subcellular compartments (Zhu, X. F., et al. (1997) *Plant Mol. Biol*. 35:331–341).

Manipulation of the corn gene in endosperm could result in increased xanthophyll content, which has value as coloring agent in poultry feed

SUMMARY OF THE INVENTION

The present invention relates to isolated polynucleotides comprising a nucleotide sequence encoding a first polypeptide of at least 35 amino acids that has at least 80% identity based on the Clustal method of alignment when compared to a corn geranylgeranyl pyrophosphate synthase polypeptide of SEQ ID NO:10. The present invention also relates to isolated polynucleotides comprising a nucleotide sequence encoding a first polypeptide of at least 50 amino acids that has at least 80% identity based on the Clustal method of alignment when compared to a polypeptide selected from the group consisting of a corn geranylgeranyl pyrophosphate synthase polypeptide of SEQ ID NO:6, and a wheat geranylgeranyl pyrophosphate synthase polypeptide of SEQ ID NO:42. The present invention also relates to isolated polynucleotides comprising a nucleotide sequence encoding a first polypeptide of at least 50 amino acids that has at least 90% identity based on the Clustal method of alignment when compared to a corn geranylgeranyl pyrophosphate synthase polypeptide of SEQ ID NO:2. The present invention also relates to isolated polynucleotides comprising a nucleotide sequence encoding a first polypeptide of at least 100 amino acids that has at least 80% identity based on the Clustal method of alignment when compared to a polypeptide selected from the group consisting of a corn geranylgeranyl pyrophosphate synthase polypeptide of SEQ ID NO:8, a rice geranylgeranyl pyrophosphate synthase polypeptide of SEQ ID NO:12, a wheat geranylgeranyl pyrophosphate synthase polypeptide of SEQ ID NO:28, a wheat geranylgeranyl pyrophosphate synthase polypeptide of SEQ ID NO:30, a rice geranylgeranyl pyrophosphate synthase polypeptide of SEQ ID NO:32, a rice geranylgeranyl pyrophosphate synthase polypeptide of SEQ ID NO:34, a soybean geranylgeranyl pyrophosphate synthase polypeptide of SEQ ID NO:36, a wheat geranylgeranyl pyrophosphate synthase polypeptide of SEQ ID NO:40 and a wheat geranylgeranyl pyrophosphate synthase polypeptide of SEQ ID NO:44. The present invention also relates to isolated polynucleotides comprising a nucleotide sequence encoding a first polypeptide of at least 100 amino acids that has at least 85% identity based on the Clustal method of alignment when compared to a polypeptide selected from the group consisting of a corn geranylgeranyl pyrophosphate synthase polypeptide of SEQ ID NO:4, a rice geranylgeranyl pyrophosphate synthase polypeptide of SEQ ID NO:14, and a soybean geranylgeranyl pyrophosphate synthase polypeptide of SEQ ID NO:20. The present invention also relates to isolated polynucleotides comprising a nucleotide sequence encoding a first polypeptide of at least 150 amino acids that has at least 80% identity based on the Clustal method of alignment when compared to a soybean geranylgeranyl pyrophosphate synthase polypeptide of SEQ ID NO:24. The present invention also relates to isolated polynucleotides comprising a nucleotide sequence encoding a first polypeptide of at least 150 amino acids that has at least 90% identity based on the Clustal method of alignment when compared to a soybean geranylgeranyl pyrophosphate synthase polypeptide of SEQ ID NO:22. The present invention also relates to isolated polynucleotides comprising a nucleotide sequence encoding a first polypeptide of at least 200 amino acids that has at least 80% identity based on the Clustal method of alignment when compared to a soybean geranylgeranyl pyrophosphate synthase polypeptide of SEQ ID NO:38. The present invention also relates to isolated polynucleotides comprising a nucleotide sequence encoding a first polypeptide of at least 200 amino acids that has at least 90% identity based on the Clustal method of alignment when compared to a soybean geranylgeranyl pyrophosphate synthase polypeptide of SEQ ID NO:18. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, and 43 that codes for the polypeptide selected from the group consisting of SEQ ID NOs:2, 4, 6, 8, 10, 12, 14, 16, 8, 20, 22, 24, 26, 28, 30, 32, 34, 36, 38, 40, 42, and 44. The present invention also relates t an isolated polynucleotide comprising a nucleotide sequences of at least 40 (preferably a least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, and 43 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a geranylgeranyl pyrophosphate synthase or a geranylgeranyl pyrophosphate synthase-related polypeptide of at least 35 amino acids comprising at least 80% homology based on the Clustal method of alignment compared to a polypeptide of SEQ ID NO:10. The present invention also relates to a geranylgeranyl pyrophosphate synthase or a geranylgeranyl pyrophosphate synthase-related polypeptide of at least 50 amino acids comprising at least 80% homology based on the Clustal method of alignment compared to a polypeptide selected from the group consisting of SEQ ID NOs:6 and 42. The present invention also relates to a geranylgeranyl pyrophosphate synthase or a geranylgeranyl pyrophosphate synthase-related polypeptide of at least 50 amino acids comprising at least 90% homology based on the Clustal method of alignment compared to a polypeptide of SEQ ID NO:2. The present invention also relates to a geranylgeranyl pyrophosphate synthase or a geranylgeranyl pyrophosphate synthase-related polypeptide of at least 100 amino acids comprising at least 80% homology based on the Clustal method of alignment compared to a polypeptide selected from the group consisting of SEQ ID NOs:8, 12, 28, 30, 32, 34, 36, 40, and 44. The present invention also relates to a geranylgeranyl pyrophosphate synthase or a geranylgeranyl pyrophosphate synthase-related polypeptide of at least 100 amino acids comprising at least 85% homology based on the Clustal method of alignment compared to a polypeptide selected from the group consisting of SEQ ID NOs:4, 14, and 20. The present invention also relates to a geranylgeranyl pyrophosphate synthase or a geranylgeranyl pyrophosphate synthase-related polypeptide of at least 100 amino acids comprising at least 90% homology based on the Clustal method of alignment compared to a polypeptide selected from the group consisting of SEQ ID NOs:16 and 26. The present invention also relates to a geranylgeranyl pyrophosphate synthase or a geranylgeranyl pyrophosphate synthase-related polypeptide of at least 150 amino acids comprising at least 80% homology based on the Clustal method of alignment compared to a polypeptide of SEQ ID NO:24. The present invention also relates to a geranylgeranyl pyrophosphate synthase or a geranylgeranyl pyrophosphate synthase-related polypeptide of at least 150 amino acids comprising at least 90% homology based on the Clustal method of alignment compared to a polypeptide of SEQ ID NO:22. The present invention also relates to a geranylgeranyl pyrophosphate synthase or a geranylgeranyl pyrophosphate synthase-related polypeptide of at least 200 amino acids comprising at least 80% homology based on the Clustal method of alignment compared to a polypeptide of SEQ ID NO:38. The present invention also relates to a geranylgeranyl pyrophosphate synthase or a geranylgeranyl pyrophosphate synthase-related polypeptide of at least 200 amino acids comprising at least 90% homology based on the Clustal method of alignment compared to a polypeptide of SEQ ID NO:18.

The present invention relates to a method of selecting an isolated polynucleotide that affects the level of expression of a geranylgeranyl pyrophosphate synthase or a geranylgeranyl pyrophosphate synthase-related polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a geranylgeranyl pyrophosphate synthase or a geranylgeranyl pyrophosphate synthase-related polypeptide in the host cell containing the isolated polynucleotide; and comparing the level of a geranylgeranyl pyrophosphate synthase or a geranylgeranyl pyrophosphate synthase-related polypeptide in the host cell containing the isolated polynucleotide with the level of a geranylgeranyl pyrophosphate synthase or a geranylgeranyl pyrophosphate synthase-related polypeptide in a host cell that does not contain the isolated polynucleotide.

The present invention relates to a method of obtaining a nucleic acid fragment encoding a substantial portion of a geranylgeranyl pyrophosphate synthase or a geranylgeranyl pyrophosphate synthase-related polypeptide gene, preferably a plant geranylgeranyl pyrophosphate synthase or a geranylgeranyl pyrophosphate synthase-related polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from Ihe group consisting of SEQ ID NOs:1, 3, 5, 7, 9, 11, 13, 15, 17, 19, 21, 23, 25, 27, 29, 31, 33, 35 37, 39, 41, and 43 and the complement of such nucleotide sequences; and amplifying a nucleic acid fragment (preferably a cDNA inserted in a cloning vector) using the oligonucleotide primer. The amplified nucleic acid fragment preferably will encode a portion of a geranylgeranyl pyrophosphate synthase or a geranylgeranyl pyrophosphate synthase-related protein amino acid sequence.

The present invention also relates to a method of obtaining a nucleic acid fragment encoding all or a substantial portion of the amino acid sequence encoding a geranylgeranyl pyrophosphate synthase or a geranylgeranyl pyrophosphate synthase-related polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a geranylgeranyl pyrophosphate synthase or a geranylgeranyl pyrophosphate synthase-related protein, the method comprising the steps of: (a) transforming a host cell with a chimeric gene comprising a nucleic acid fragment encoding a geranylgeranyl pyrophosphate synthase or a geranylgeranyl pyrophosphate synthase-related protein, operably linked to suitable regulatory sequences; (b) growing the transformed host cell under conditions that are suitable for expression of the chimeric gene wherein expression of the chimeric gene results in production of geranylgeranyl pyrophosphate synthase or a geranylgeranyl pyrophosphate synthase-related protein in the transformed host cell; (c) optionally purifying the geranylgeranyl pyrophosphate synthase or a geranylgeranyl pyrophosphate synthase-related protein expressed by the transformed host cell; (d) treating the geranylgeranyl pyrophosphate synthase or a geranylgeranyl pyrophosphate synthase-related protein with a compound to be tested; and (e) comparing the activity of the geranylgeranyl pyrophosphate synthase or a geranylgeranyl pyrophosphate synthase-related protein that has been treated with a test compound to the activity of an untreated geranylgeranyl pyrophosphate synthase or a geranylgeranyl pyrophosphate synthase-related protein, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B depicts the amino acid alignment between the geranylgeranyl pyrophosphate synthase encoded by the nucleotide sequences derived from soybean clone sdc5c.pk0003.e4 (SEQ ID NO:18), soybean clone sdp2c.pk005.h19 (SEQ ID NO:22), soybean clone sfl1.pk125.k18 (SEQ ID NO:26), and a geranylgeranyl pyrophosphate synthase-encoding nucleic acid fragment from *Lupinus albus* (NCBI General Identification No. 558925) (SEQ ID NO:45). Amino acids which are conserved among all and at least two sequences with an amino acid at that position are indicated with an asterisk (*) above them. Dashes are used by the program to maximize alignment of the sequences.

FIGS. 2A and 2B depicts the amino acid alignment between the geranylgeranyl pyrophosphate synthase-related protein encoded by the nucleotide sequences derived from rice clone r10n.pk0060.e7 (SEQ ID NO:34), soybean clone sfl1.pk126.o24 (SEQ ID NO:38), wheat clone wle1n.pk0075.a12 ( SEQ ID NO:44), and a geranylgeranyl pyrophosphate synthase-related protein-encoding nucleic acid fragment from *Arabidopsis thaliana* (NCBI General Identification No. 4467133) (SEQ ID NO:46). Amino acids which are conserved among all and at least two sequences with an amino acid at that position are indicated with an asterisk (*) above them. Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide SEQ ID NOs:1, 5, 11, 15, 19, 23, 27, 31, 35, 39, and 41 correspond to nucleotide SEQ ID NOs:1, 3, 5, 7, 9, 11, 13, 15, 17, 19, and 21, respectively, presented in U.S. Provisional Application No. 60/110,592, filed Dec. 2, 1998. Amino acid SEQ ID NOs:2, 6, 12, 16, 20, 24, 28, 32, 36, 40, and 42 correspond to amino acid SEQ ID NOs:2, 4, 6, 8, 10, 12, 14, 16, 18, 20, and 22, respectively presented in U.S. Provisional Application No. 60/110,592, filed Dec. 2, 1998. The sequence descriptions and Sequence Listing attached hereto comply with the rules governing nucleotide and/or amino acid sequence disclosures in patent applications as set forth in 37 C.F.R. §1.821–1.825.

TABLE 1

Geranylgeranyl Pyrophosphate (GGPP) Synthases

| | | | SEQ ID NO: | |
|---|---|---|---|---|
| Protein | Clone Designation | Status | (Nucleotide) | (Amino Acid) |
| GGPP Synthase (Corn) | cco1n.pk0015.b1 | EST | 1 | 2 |
| GGPP Synthase (Corn) | cco1n.pk0015.b1 | FIS | 3 | 4 |
| GGPP Synthase (Corn) | cta1n.pk0070.a6 | EST | 5 | 6 |
| GGPP Synthase (Corn) | cta1n.pk0070.a6 | FIS | 7 | 8 |
| GGPP Synthase (Corn) | p0120.cdeae73r | FIS | 9 | 10 |
| GGPP Synthase (Rice) | r10n.pk084.f7 rr1.pk0048.f9 | Contig | 11 | 12 |
| GGPP Synthase (Rice) | r10n.pk084.f7 | FIS | 13 | 14 |
| GGPP Synthase (Soybean) | sdc5c.pk0003.e4 sgs4c.pk005.j3 se3.05h07 sf11.pk0001.a11 | Contig | 15 | 16 |
| GGPP Synthase (Soybean) | sdc5c.pk0003.e4 | CGS | 17 | 18 |
| GGPP Synthase (Soybean) | sdp2c.pk005.h19 sf11.pk127.f10 sdc2c.pk001.i19 | Contig | 19 | 20 |
| GGPP Synthase (Soybean) | sdp2c.pk005.h19 | CGS | 21 | 22 |

TABLE 1-continued

Geranylgeranyl Pyrophosphate (GGPP) Synthases

| | | | SEQ ID NO: | |
|---|---|---|---|---|
| Protein | Clone Designation | Status | (Nucleotide) | (Amino Acid) |
| GGPP Synthase (Soybean) | sf11.pk125.k18<br>srr1c.pk003.i24<br>sf11.pk0043.d11<br>sdp4c.pk002.o22 | Contig | 23 | 24 |
| GGPP Synthase (Soybean) | sf11.pk125.k18 | CGS | 25 | 26 |
| GGPP Synthase (Wheat) | Contig of:<br>wr1.pk0001.a2<br>w1e1n.pk0101.a3<br>wr1.pk0138.a12 | Contig | 27 | 28 |
| GGPP Synthase (Wheat) | Contig of:<br>w11n.pk0035.g9<br>wr1.pk0001.a2 | Contig* | 29 | 30 |
| GGPP Synthase-Related Protein (Rice) | r10n.pk0060.e7 | EST | 31 | 32 |
| GGPP Synthase-Related Protein (Rice) | r10n.pk0060.e7 | CGS | 33 | 34 |
| GGPP Synthase-Related Protein (Soybean) | Contig of:<br>sf11.pk126.o24<br>s12.pk126.l19 | Contig | 35 | 36 |
| GGPP Synthase-Related Protein (Soybean) | sf11.pk126.o24 | CGS | 37 | 38 |
| GGPP Synthase-Related Protein (Wheat) | Contig of:<br>w1e1n.pk0075.a12<br>w1m12.pk0002.a4 | Contig | 39 | 40 |
| GGPP Synthase-Related Protein (Wheat) | w1m24.pk0016.c6 | EST | 41 | 42 |
| GGPP Synthase-Related Protein (Wheat) | w1e1n.pk0075.a12 | CGS | 43 | 44 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized, As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides, of the nucleic acid sequence of the SEQ ID NOs:1, 3, 5, 7, 9, 11, 13, 15, 17, 19, 21, 23, 25, 27, 29, 31, 33, 35, 37, 39, 41, 43, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level f the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not hare 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting SEQ ID NOs:1, 3, 5, 7, 9, 11, 13, 15, 17, 19, 21, 23, 25, 27, 29, 31, 33, 35, 37, 39, 41, 43, and the complement of such nucleotide sequences may be used in methods of selecting an isolated polynucleotide that affects the expression of a polypeptide (such as a GGPP synthase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short cligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several geranylgeranyl pyrophosphate synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other geranylgeranyl pyrophosphate synthase or a geranylgeranyl pyrophosphate synthase-related protein, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragment encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. A cad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as geranylgeranyl pyrophosphate synthase or a geranylgeranyl pyrophosphate synthase-related protein) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (such as GGPP synthase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of geranylgeranyl pyrophosphate in those cells. Increasing the amount of GGPP synthase in the plant cell may result in increased amounts of carotenoids yielding brighter colors in the flower and the fruit and higher levels of beta-carotene as well as other terpenoids derived from geranylgeranyl pyrophosphate. The polypeptides disclosed herein may also be used as targets for herbicide discovery since geranylgeranyl pyrophosphate is precursor to many metabolites important for plant viability including phytohormone, defence-substances, and photosynthetic pigments.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) Mol Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded geranylgeranyl pyrophosphate synthase. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze steps in isoprenoid biosynthesis. Geranylgeranyl pyrophosphate synthase specifically is the enzyme responsible for the formation of geranylgeranyl pyrophosphate which is the precursor for important molecules such as phytohormones, photosynthetic pigments (carotenoids), and defense-related substances (phytoalexins and toxins). Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding geranylgeranyl pyrophosphate synthases were identfied by conducting BLAST (Basic Local Alignment Search Tool; Altschul et al. (1993) *J. Mol. Biol.* 215:403–410) searches for similarity to sequences

TABLE 2 cDNA Libraries from Corn, Rice, Soybean and Wheat

| Library | Tissue | Clone |
|---|---|---|
| cco1n | Corn Cob of 67 Day Old Plants Grown in Green House* | cco1n.pk0015.b1 |
| cta1n | Corn Tassel* | cta1n.pk0070.a6 |
| p0120 | Pooled Corn Endosperm: 18, 21, 24, 27 and 29 Days After Pollination, Screened 1 | p0120.cdeae73r |
| r10n | Rice 15 Day Old Leaf* | r10n.pk0060.e7 |
|  |  | r10n.pk084.f7 |
| rr1 | Rice Root of Two Week Old Developing Seedling | rr1.pk0048.f9 |
| sdc2c | Soybean Developing Cotyledon (6–7 mm) | sdc2c.pk001.i19 |
| sdc5c | Soybean Developing Cotyledon (10–12 mm) | sdc5c.pk0003.e4 |
| sdp2c | Soybean Developing Pod (6–7 mm) | sdp2c.pk005.h19 |
| sdp4c | Soybean Developing Pod (10–12 mm) | sdp4c.pk002.o22 |
| se3 | Soybean Embryo, 17 Days After Flowering | se3.05h07 |
| sfl1 | Soybean Immature Flower | sfl1.pk0001.a11 |
|  |  | sfl1.pk0043.d11 |
|  |  | sfl1.pk125.k18 |
|  |  | sfl1.pk126.o24 |
|  |  | sfl1.pk127.f10 |
| sgs4c | Soybean Seed 2 Days After Germination | sgs4c.pk005.j3 |
| s12 | Soybean Two-Week-Old Developing Seedling Treated With 2.5 ppm chlorimuron | s12.pk126.119 |
| srr1c | Soybean 8 Day Old Root | srr1c.pk003.i24 |
| wl1n | Wheat Leaf From 7 Day Old Seedling Light Grown* | wl1n.pk0035.g9 |
| wle1n | Wheat Leaf From 7 Day Old Etiolated Seedling* | wle1n.pk0075.a12 |
|  |  | wle1n.pk0101.a3 |
| w1m12 | Wheat Seedling 12 Hours After Inoculation With *Erysiphe graminis f. sp tritici* | w1m12.pk0002.a4 |
| w1m24 | Wheat Seedling 24 Hours After Inoculation With *Erysiphe graminis f. sp tritici* | w1m24.pk0016.c6 |
| wr1 | Wheat Root From 7 Day Old Seedling Light Grown | wr1.pk0001.a2 |
|  |  | wr1.pk0138.a12 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Geranylgeranyl Pyrophosphate Synthase

The BLASTX search using the EST sequence from clone cco1n.pk0015.b1, the nucleotide sequence of the contig assembled from clones sdc5c.pk0003.e4, sgs4c.pk005.j3, se3.05h07 and sfl1.pk0001.a11, the nucleotide sequence of the contig assembled from clones sdp2c.pk005.h19, sfl1.pk127.f10 and sdc2c.pk001.i19, the nucleotide sequence of th contig assembled from clones sfl1.pk125.k18, srr1c.pk003.i24, sfl1.pk0043.d11 and sdp4c.pk002.o22 and the nucleotide sequence of the contig assembled from clones wr1.pk0001.a2, w1e1n.pk0101.a3 and wr1.pk0138.a12 revealed similarity of the protei encoded by the cDNAs to geranylgeranyl pyrophosphate synthase from *Lupinus albus* and *Arabidopsis thaliana* (NCBI gi Accession Nos. 558925 and 2464899, respectively). The BLAST results for each of these sequences are shown in Table 3:

TABLE 3

BLAST Results for Clones Encoding Polypeptides Homologous to Geranylgeranyl Pyrophosphate Synthase

| | BLAST pLog Score | |
|---|---|---|
| Clone | 558925 | 2464899 |
| cco1n.pk0015.b1 | 29.15 | 32.70 |
| Contig of: | 106.00 | 83.52 |
| sdc5c.pk0003.e4 | | |
| sgs4c.pk005.j3 | | |
| se3.05h07 | | |
| sfl1.pk0001.a11 | | |
| Contig of: | 54.69 | 56.00 |
| sdp2c.pk005.h19 | | |
| sfl1.pk127.f10 | | |
| sdc2c.pk001.i19 | | |
| Contig of: | 60.70 | 58.70 |
| sfl1.pk125.k18 | | |
| srr1c.pk003.i24 | | |
| sfl1.pk0043.d11 | | |
| sdp4c.pk002.o22 | | |
| Contig of: | 51.52 | 55.30 |
| wr1.pk0001.a2 | | |
| w1e1n.pk0101.a3 | | |
| wr1.pk0138.a12 | | |

The BLASTX search using the EST sequence from clone cta1n.pk0070.a6 and the nucleotide sequence from the contig assembled from clones r10n.pk084.f7 and rr1.pk0048.f9 revealed similarity of the proteins encoded by the cDNAs to geranylgeranyl pyrophosphate synthetase precursor from *Arabidopsis thaliana* (NCBI gi Accession No. 462174) with pLog values of 39.70 and 89.00, respectively.

The sequence of a portion of the cDNA insert from clone cco1n.pk0015.b1 is shown in SEQ ID NO:1; the deduced amino acid sequence of this cDNA is shown in SEQ ID NO:2. The sequence of a portion of the cDNA insert from clone cta1n.pk00700.a6 is shown in SEQ ID NO:5; the deduced amino acid sequence of this cDNA is shown in SEQ ID NO:6. The sequence of a contig assembled of the cDNA insert from clones r10n.pk084.f7 and rr1.pk0048.f9 is shown in SEQ ID NO:11; the deduced amino acid sequence of this contig is shown in SEQ ID NO:12. The sequence of a contig assembled of the cDNA insert from clones sdc5c.pk0003.e4, sgs4c.pk005j3, se3.05h07 and sfl1.pk0001.a11 is shown ID NO:15; the deduced amino acid sequence of this contig is shown in SEQ ID NO:16. The sequence of a contig assembled of the cDNA insert from clones sdp2c.pk005.h19, sfl1.pk127.f10 and sdc2c.pk001.i19 is shown in SEQ ID NO:19; the deduced amino acid sequence of this contig is shown in SEQ ID NO:20. The sequence of a contig assembled of the cDNA insert from clones sfl1.pk125.k18, srr1c.pk003.i24, sfl1.pk0043.d11 and sdp4c.pk002.o22 is shown in SEQ ID NO:23; the deduced amino acid sequence of this contig is shown in SEQ ID NO:24. The sequence of a contig assembled of the cDNA insert from clone wr1.pk0001.a2, w1e1n.pk0101.a3 and wr1.pk0138.a12 is shown in SEQ ID NO:27; the deduced amino acid sequence of this contig is shown in SEQ ID NO:28. BLAST scores and probabilities indicate that the instant nucleic acid fragments encode portions of corn, rice, soybean and wheat geranylgeranyl pyrophosphate synthase. These sequences represent the first monocot and the first soybean sequences encoding geranylgeranyl pyrophosphate synthase.

The BLASTX search using the sequences from clones listed in Table 4 revealed similarity of the polypeptides encoded by the cDNAs to geranylgeranyl pyrophosphate synthase from different plant species including *Sinapis alba* (NCBI General Identification No. 1419758), *Oryza sativa* (NCBI General Identification No. 5042458), *Catharanthus roseus* (NCBI General Identification No. 1063276), and *Lupinus albus* (NCBI General Identification No. 558925). Shown in Table 4 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Geranylgeranyl Pyrophosphate Synthase

| | | BLAST Results | |
|---|---|---|---|
| Clone | Status | NCBI General Identification No. | pLog Score |
| cco1n.pk0015.b1 | FIS | 1419758 | 49.40 |
| cta1n.pk0070.a6 | FIS | 5042458 | 51.70 |
| p0120.cdeae73r | FIS | 1063276 | 5.00 |
| r10n.pk084.f7 | FIS | 1419758 | 85.30 |
| sdc5c.pk0003.e4 | CGS | 1063276 | 138.00 |
| sdp2c.pk005.h19 | CGS | 558925 | 140.00 |
| sfl1.pk125.k18 | CGS | 558925 | 144.00 |
| Contig of: w11n.pk0035.g9 wr1.pk0001.a2 | Contig* | 1419758 | 73.52 |

FIGS. 1A and 1B presents an alignment of the amino acid sequences set forth in SEQ ID NOs:18, 22, and 26 and the *Lupinus albus* sequence (NCBI General Identification No. 558925) (SEQ ID NO:45). The data in Table 5 represents a calculation of the percent identity of the amino acid sequences set forth in SEQ ID NOs:18, 22, and 26 and the *Lupinus albus* sequence (NCBI General Identification No. 558925) (SEQ ID NO:45).

TABLE 5

Percent Identity of Amino Acid Sequences Deduced From the Nucleotide Sequences of cDNA Clones Encoding Polypeptides Homologous to Geranylgeranyl Pyrophosphate Synthase

| SEQ ID NO. | Percent Identity to NCBI General Identification No. 558925 |
| --- | --- |
| 18 | 74.7 |
| 22 | 77.5 |
| 26 | 80.1 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode all or a substantial portion of geranylgeranyl pyrophosphate synthase.

Example 4

Characterization of cDNA Clones Encoding Geranylgeranyl Pyrophosphate Synthase-Related Protein The BLASTX search using the EST sequences from clones r10n.pk0060.e7 and w1m24.pk0016.c6, the nucleotide sequence of the contig assembled from clones sfl1.pk126.o24 and s12.pk126.119 and the nucleotide sequence of the contig assembled from clones w1e1n.pk0075.a12 and w1m12.pk0002.a4 revealed similarity of the proteins encoded by the cDNAs to geranylgeranyl pyrophosphate synthase-related protein from *Arabidopsis thaliana* (NCBI gi Accession No. 735880). The BLAST results for each of these sequences are shown in Table 6:

TABLE 6

BLAST Results for Clones Encoding Polypeptides Homologous to Geranylgeranyl Pyrophosphate Synthase-Related Protein

| Clone | BLAST pLog Score 735880 |
| --- | --- |
| r10n.pk0060.e7 | 24.30 |
| Contig of: | 30.30 |
| sf1.pk126.o24 | |
| s12.pk126.119 | |
| Contig of: | 15.15 |
| w1e1n.pk0075.a12 | |
| w1m12.pk0002.a4 | |
| w1m24.pk0016.c6 | 23.05 |

The sequence of a portion of the cDNA insert from clone r10n.pk0060.e7 is shown in SEQ ID NO:31; the deduced amino acid sequence of this cDNA is shown in SEQ ID NO:32. The sequence of a contig assembled of the cDNA insert from clones sfl1.pk126.o24 and s12.pk126.119 is shown in SEQ ID NO:35; the deduced amino acid sequence of this contig is shown in SEQ ID NO:36. The sequence of a contig assembled of the cDNA insert from clones w1e1n.pk0075.a12 and w1m2.pk0002.a4 is shown in SEQ ID NO:39; the deduced amino acid sequence of this contig is shown in SEQ ID NO:40. The sequence of a portion of the cDNA insert from clone w1m24.pk0016.c6 is shown in SEQ ID NO:41; the deduced amino acid sequence of this cDNA is shown in SEQ ID NO:42. BLAST scores and probabilities indicate that the instant nucleic acid fragments encode portions of rice, soybean and wheat geranylgeranyl pyrophosphate synthase-related protein. These sequences represent the first monocot and the first soybean sequences encoding geranylgeranyl pyrophosphate synthase-related protein.

The BLASTX search using the sequences from clones listed in Table 7 revealed similarity of the polypeptides encoded by the cDNAs to geranylgeranyl pyrophosphate synthase-related protein from *Arabidopsis thaliana* (NCBI General Identification Nos. 735880 and 4467133). Shown in Table 7 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 7

BLAST Results for Sequences Encoding Polypeptides Homologous to Geranylgeranyl Pyrophosphate Synthase-Related Protein

| | | BLAST Results | |
| --- | --- | --- | --- |
| Clone | Status | NCBI General Identification No. | pLog Score |
| r10n.pk0060.e7 | CGS | 735880 | 85.70 |
| sf11.pk126.o24 | CGS | 4467133 | 112.00 |
| w1e1n.pk0075.a12 | CGS | 735880 | 86.05 |

FIGS. 2A and 2B presents an alignment of the amino acid sequences set forth in SEQ ID NOs:34, 38, and 44 and the *Arabidopsis thaliana* sequence (NCBI General Identification No. 4467133) (SEQ ID NO:46). The data in Table 8 represents a calculation of the percent identity of the amino acid sequences set forth in SEQ ID NOs:34, 38, and 44 and the *Arabidopsis thaliana* sequence (NCBI General Identification No. 4467133) (SEQ ID NO:46).

TABLE 8

Percent Identity of Amino Acid Sequences Deduced From the Nucleotide Sequences of cDNA Clones Encoding Polypeptides Homologous to Geranylgeranyl Pyrophosphate Synthase-Related Protein

| SEQ ID NO. | Percent Identity to NCBI General Identification No. 4467133 |
| --- | --- |
| 34 | 47.5 |
| 38 | 60.7 |
| 44 | 47.5 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode all or a substantial portion of a geranylgeranyl pyrophosphate synthase-related protein.

Example 5

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kaptonm flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Geranylgeranyl Pyrophosphate Synthase The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for geranylgeranyl pyrophosphate synthase are presented by G. E. Bartley, et al. (1992) *J. Biol. Chem.* 267:5036–5039.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having geranylgeranyl pyrophosphate synthase activity, wherein the amino acid sequence of the polypeptide and the amino acid sequence of SEQ ID NO:38 have at least 90% sequence identity, or
   (b) the complement of the nucleotide sequence, wherein the complement and the nucleotide sequence contain the same number of nucleotides and are 100% complementary.

2. The polynucleotide of claim 1 wherein the sequence identity is at least 95%.

3. The polynucleotide of claim 1 wherein the polynucleotide encodes the polypeptide of SEQ ID NO:38.

4. The polynucleotide of claim 1 that comprises the nucleotide sequence of SEQ ID NO:37.

5. A recombinant DNA construct comprising the polynucleotide of claim 1 operably linked to at least one regulatory sequence.

6. A cell comprising the polynucleotide of claim 1.

7. The cell of claim 1, wherein the cell is selected from the group consisting of a yeast cell, a bacterial cell and a plant cell.

8. A transgenic plant comprising the polynucleotide of claim 1.

9. A virus comprising the polynucleotide of claim 1.

10. A method for transforming a cell comprising introducing into a cell the polynucleotide of claim 1.

11. A method for producing a transgenic plant comprising (a) transforming a plant cell with the polynucleotide of claim 1 and (b) regenerating a transgenic plant from the transformed plant cell.

12. A vector comprising the polynucleotide of claim 1.

13. A seed comprising the recombinant DNA construct of claim 5.

* * * * *

SEQUENCE LISTING

<160> NUMBER OF SEQ ID NOS: 46

<210> SEQ ID NO 1
<211> LENGTH: 553
<212> TYPE: DNA
<213> ORGANISM: Zea mays
<220> FEATURE:
<221> NAME/KEY: unsure
<222> LOCATION: (429)
<221> NAME/KEY: unsure
<222> LOCATION: (435)
<221> NAME/KEY: unsure
<222> LOCATION: (443)
<221> NAME/KEY: unsure
<222> LOCATION: (449)
<221> NAME/KEY: unsure
<222> LOCATION: (465)
<221> NAME/KEY: unsure
<222> LOCATION: (494)

```
<221> NAME/KEY: unsure
<222> LOCATION: (503)
<221> NAME/KEY: unsure
<222> LOCATION: (536)

<400> SEQUENCE: 1
atcagagacg gtgcccctcg aacgcctcga gtacatccac ctccacaaga ccgccgcatt      60
gctcgaggcc tcggtggtga ttggggcgat catcggaggc ggcacggacg agcagatcga     120
gaggctgcgg aagtacgcga ggtcgatcgg gctgctgttc caggtggtcg acgacatact     180
cgatgtcacc aagtcgtcag aggagctcga aaaaccggcg gggaaaggac ctggcaagcg     240
acaaaacgac gtacccgaag ctgctggggc tagaaaatcg cgggattcgc ggaggattgc     300
tctctgatcc gttagagcac ttgcttgctt cgacaaggag aaggaacgcc tctgttcatc     360
tggcaactat atcgcccata ggcagaactg agaattttag gtactgcgta tctatgtccg     420
actgttgtnc ttgtnaagcc tcnccctcna actgggttcc agganatacc aatctcaagt     480
gagtaacaac ttanccgtc ctnatgaagg gcgttaattc aatcaaagat gatacnacaa      540
tttgaaaaaa gaa                                                       553

<210> SEQ ID NO 2
<211> LENGTH: 72
<212> TYPE: PRT
<213> ORGANISM: Zea mays

<400> SEQUENCE: 2

Val Pro Leu Glu Arg Leu Glu Tyr Ile His Leu His Lys Thr Ala Ala
 1               5                  10                  15

Leu Leu Glu Ala Ser Val Val Ile Gly Ala Ile Ile Gly Gly Gly Thr
            20                  25                  30

Asp Glu Gln Ile Glu Arg Leu Arg Lys Tyr Ala Arg Ser Ile Gly Leu
        35                  40                  45

Leu Phe Gln Val Val Asp Asp Ile Leu Asp Val Thr Lys Ser Ser Glu
    50                  55                  60

Glu Leu Glu Lys Pro Ala Gly Lys
 65                  70

<210> SEQ ID NO 3
<211> LENGTH: 644
<212> TYPE: DNA
<213> ORGANISM: Zea mays

<400> SEQUENCE: 3
gcacgagatc agagacggtg cccctcgaac gcctcgagta catccacctc cacaagaccg      60
ccgcattgct cgaggcctcg gtggtgattg ggcgatcat cggaggcggc acggacgagc     120
agatcgagag gctgcggaag tacgcgaggt cgatcgggct gctgttccag gtggtcgacg     180
acatactcga tgtcaccaag tcgtcagagg agctcggcaa gacggcgggg aaggacctgg     240
caagcgacaa aacgacgtac ccgaagctgc tggggctaga aaagtcgcgg gagttcgcgg     300
aggagttgct ctctgatgcc gtagagcagc ttgcttgctt cgacaaggag aaggcagcgc     360
ctctgttgca tctggccaac tatatcgccc ataggcagaa ctgagaattt gaggtgactg     420
cgtactctat tgtcggacct gttgtgactt tgtcaggcct cgcccgtcg aacttgggtt      480 cgaggaatat atccaaatcg tcatgtgatg tatactagct gtagctctgt accttgatgg     540 aatgggctg tttagttcga attccaaaag tatgaaatat cgtatcaaat tatgaaaaaa     600
aaaaaaaaaa aaaaaaaaaa aaaaaaaaaa aaaaaaaaaa aaaa                     644
```

<210> SEQ ID NO 4
<211> LENGTH: 133
<212> TYPE: PRT
<213> ORGANISM: Zea mays

<400> SEQUENCE: 4

Thr Arg Ser Glu Thr Val Pro Leu Glu Arg Leu Glu Tyr Ile His Leu
 1               5                  10                  15

His Lys Thr Ala Ala Leu Leu Glu Ala Ser Val Val Ile Gly Ala Ile
            20                  25                  30

Ile Gly Gly Gly Thr Asp Glu Gln Ile Glu Arg Leu Arg Lys Tyr Ala
        35                  40                  45

Arg Ser Ile Gly Leu Leu Phe Gln Val Val Asp Asp Ile Leu Asp Val
    50                  55                  60

Thr Lys Ser Ser Glu Glu Leu Gly Lys Thr Ala Gly Lys Asp Leu Ala
65                  70                  75                  80

Ser Asp Lys Thr Thr Tyr Pro Lys Leu Leu Gly Leu Glu Lys Ser Arg
                85                  90                  95

Glu Phe Ala Glu Glu Leu Leu Ser Asp Ala Val Glu Gln Leu Ala Cys
            100                 105                 110

Phe Asp Lys Glu Lys Ala Ala Pro Leu Leu His Leu Ala Asn Tyr Ile
        115                 120                 125

Ala His Arg Gln Asn
    130

<210> SEQ ID NO 5
<211> LENGTH: 530
<212> TYPE: DNA
<213> ORGANISM: Zea mays
<220> FEATURE:
<221> NAME/KEY: unsure
<222> LOCATION: (341)
<221> NAME/KEY: unsure
<222> LOCATION: (347)
<221> NAME/KEY: unsure
<222> LOCATION: (469)
<221> NAME/KEY: unsure
<222> LOCATION: (492)
<221> NAME/KEY: unsure
<222> LOCATION: (497)
<221> NAME/KEY: unsure
<222> LOCATION: (501)
<221> NAME/KEY: unsure
<222> LOCATION: (530)

<400> SEQUENCE: 5
aggtcgccga catggcgagc gagggagccc cctccggctc cgtgagcctg ggcgcgctgg      60
agtacatcca tgtgcacaag actgcgcggc tcgtggaggc cgcggccgtg tcgggcgccg     120
tcgtcggggg cggggcgac ggcgaggtcg agcgcgtccg tcggtacgcg cacttcttag      180
ggctcctggg ccaggtggtg gacgacgttc tggacgtgac gggcacgtcg gagcagctcg     240
ggaagacggc gggcaaggac gttgccgccg gcaaggccac gtaccacgg ctgatgggct      300 taaagggagc gcgcgcatac atgggcgagc tcctggcgaa ngccgangcg gagctcgacg     360
ggttggacgc cgcgcgcacg gcgccgctgc ggcacctcgc gcggttatgg ccacagacag     420
cattgagatg gggtggaagt ggaactatgg attggtctgg ccggctaanc ggaacactta     480
taaaatgatg cntgacnata nttctaaact caacaacgag tatttcttan              530

<210> SEQ ID NO 6

```
<211> LENGTH: 133
<212> TYPE: PRT
<213> ORGANISM: Zea mays
<220> FEATURE:
<221> NAME/KEY: UNSURE
<222> LOCATION: (113)
<221> NAME/KEY: UNSURE
<222> LOCATION: (115)

<400> SEQUENCE: 6
```

| | | | | | | | | | | | | | | | |
|---|---|---|---|---|---|---|---|---|---|---|---|---|---|---|---|
| Val | Ala | Asp | Met | Ala | Ser | Glu | Gly | Ala | Pro | Ser | Gly | Ser | Val | Ser | Leu |
| 1 | | | | 5 | | | | | 10 | | | | | 15 | |

| | | | | | | | | | | | | | | |
|---|---|---|---|---|---|---|---|---|---|---|---|---|---|---|
| Gly | Ala | Leu | Glu | Tyr | Ile | His | Val | His | Lys | Thr | Ala | Arg | Leu | Val | Glu |
| | | | 20 | | | | | 25 | | | | | 30 | | |

| | | | | | | | | | | | | | | | |
|---|---|---|---|---|---|---|---|---|---|---|---|---|---|---|---|
| Ala | Ala | Ala | Val | Ser | Gly | Ala | Val | Val | Gly | Gly | Gly | Asp | Gly | Glu |
| | | 35 | | | | | 40 | | | | | 45 | | | |

| | | | | | | | | | | | | | | | |
|---|---|---|---|---|---|---|---|---|---|---|---|---|---|---|---|
| Val | Glu | Arg | Val | Arg | Arg | Tyr | Ala | His | Phe | Leu | Gly | Leu | Leu | Gly | Gln |
| | 50 | | | | | 55 | | | | | 60 | | | | |

| | | | | | | | | | | | | | | | |
|---|---|---|---|---|---|---|---|---|---|---|---|---|---|---|---|
| Val | Val | Asp | Asp | Val | Leu | Asp | Val | Thr | Gly | Thr | Ser | Glu | Gln | Leu | Gly |
| 65 | | | | | 70 | | | | | 75 | | | | | 80 |

| | | | | | | | | | | | | | | | |
|---|---|---|---|---|---|---|---|---|---|---|---|---|---|---|---|
| Lys | Thr | Ala | Gly | Lys | Asp | Val | Ala | Ala | Gly | Lys | Ala | Thr | Tyr | Pro | Arg |
| | | | | 85 | | | | | 90 | | | | | 95 | |

| | | | | | | | | | | | | | | | |
|---|---|---|---|---|---|---|---|---|---|---|---|---|---|---|---|
| Leu | Met | Gly | Leu | Lys | Gly | Ala | Arg | Ala | Tyr | Met | Gly | Glu | Leu | Leu | Ala |
| | | | | 100 | | | | | 105 | | | | | 110 | |

| | | | | | | | | | | | | | | | |
|---|---|---|---|---|---|---|---|---|---|---|---|---|---|---|---|
| Xaa | Ala | Xaa | Ala | Glu | Leu | Asp | Gly | Leu | Asp | Ala | Ala | Arg | Thr | Ala | Pro |
| | 115 | | | | | 120 | | | | | 125 | | | | |

| | | | |
|---|---|---|---|
| Leu | Arg | His | Leu | Ala |
| | 130 | | | |

```
<210> SEQ ID NO 7
<211> LENGTH: 568
<212> TYPE: DNA
<213> ORGANISM: Zea mays

<400> SEQUENCE: 7
gcacgagagg tcgccgacat ggcgagcgag ggagccccct ccggctccgt gagcctgggc      60
gcgctggagt acatccatgt gcacaagact gcgcggctcg tggaggccgc ggccgtgtcg     120
ggcgccgtcg tcgggggcgg gggcgacggc gaggtcgagc gcgtccgtcg gtacgcgcac     180
ttcttagggc tcctgggcca ggtggtggac gacgttctgg acgtgacggg cacgtcggag     240
cagctcggga agacggcggg caaggacgtt gccgccggca aggccacgta cccacggctg     300
atgggcttaa agggagcgcg cgcatacatg ggcgagctcc tggcgaaggc cgaggcggag     360
ctcgacgggt tggacgccgc gcgcacggcg ccgctgcggc acctcgcgcg gttcatggcg     420
cacagacagc attgagatgg ggtggaagtg gaactatgga agtggatctg gccggctcat     480
ccggaacact tgataaaagt gatgcgttga ctattagttt ctcagacctc aacatcgagt     540
gattacttta aaaaaaaaaa aaaaaaaa                                        568

<210> SEQ ID NO 8
<211> LENGTH: 142
<212> TYPE: PRT
<213> ORGANISM: Zea mays

<400> SEQUENCE: 8
```

| | | | | | | | | | | | | | | | |
|---|---|---|---|---|---|---|---|---|---|---|---|---|---|---|---|
| Glu | Val | Ala | Asp | Met | Ala | Ser | Glu | Gly | Ala | Pro | Ser | Gly | Ser | Val | Ser |
| 1 | | | | 5 | | | | | 10 | | | | | 15 | |

| | | | | | | | | | | | | | | | |
|---|---|---|---|---|---|---|---|---|---|---|---|---|---|---|---|
| Leu | Gly | Ala | Leu | Glu | Tyr | Ile | His | Val | His | Lys | Thr | Ala | Arg | Leu | Val |
| | | | 20 | | | | | 25 | | | | | 30 | | |

```
Glu Ala Ala Ala Val Ser Gly Ala Val Gly Gly Gly Asp Gly
         35                  40                  45

Glu Val Glu Arg Val Arg Arg Tyr Ala His Phe Leu Gly Leu Leu Gly
     50                  55                  60

Gln Val Val Asp Asp Val Leu Asp Val Thr Gly Thr Ser Glu Gln Leu
 65                  70                  75                  80

Gly Lys Thr Ala Gly Lys Asp Val Ala Gly Lys Ala Thr Tyr Pro
             85                  90                  95

Arg Leu Met Gly Leu Lys Gly Ala Arg Ala Tyr Met Gly Glu Leu Leu
            100                 105                 110

Ala Lys Ala Glu Ala Glu Leu Asp Gly Leu Asp Ala Ala Arg Thr Ala
        115                 120                 125

Pro Leu Arg His Leu Ala Arg Phe Met Ala His Arg Gln His
        130                 135                 140
```

<210> SEQ ID NO 9
<211> LENGTH: 365
<212> TYPE: DNA
<213> ORGANISM: Zea mays

<400> SEQUENCE: 9

```
ccacgcgtcc ggagaagttg gtctctgacg caacagagca gctcgcttgc ttcgacgagg      60
agaaggcagc acccctgttg cacttggcca actatatcgc ccacaggcag aactgaagat     120
ttgtggtgat gcttattctg ttcttgctca ctgtcgatct gtaacattgt ataaggcagt     180
tgatattggt tctgagaaat atttccaaat cgtcatttgg tgtatactag ctgtagctct     240
gtaccttgat gtaatgaggc tgttatattt ttttctcca ttgaagaatg caaataaata      300
tggaaaaaaa aaaaaaaaaa aaaaaaaaaa aaaaaaaaaa aaaaaaaaaa aaaaaaaaaa     360
aaaag                                                                 365
```

<210> SEQ ID NO 10
<211> LENGTH: 37
<212> TYPE: PRT
<213> ORGANISM: Zea mays

<400> SEQUENCE: 10

```
Thr Arg Pro Glu Lys Leu Val Ser Asp Ala Thr Glu Gln Leu Ala Cys
  1               5                  10                  15

Phe Asp Glu Glu Lys Ala Ala Pro Leu Leu His Leu Ala Asn Tyr Ile
             20                  25                  30

Ala His Arg Gln Asn
         35
```

<210> SEQ ID NO 11
<211> LENGTH: 973
<212> TYPE: DNA
<213> ORGANISM: Oryza sativa
<220> FEATURE:
<221> NAME/KEY: unsure
<222> LOCATION: (445)

<400> SEQUENCE: 11

```
cttacagcac accatgtcgc tcgtccacga cgacctcccc tgcatggacg acgacgacct      60
ccgccgcggg aagcccacct gccacgtcgt ctacggggag cccatcgccg tgctcaccgg     120
cgacgcgctg ctctccctct ccttccacca catggccagg ttcgactcct accctccgga     180
catcgacgct gacaagcacc ccgcccgcgt cgtccgcgcc attggcgagc tcgcgcgctg     240
```

-continued

```
cataggctcc gagggcctag tcgccggcca ggttgttgat cttgagatga ctggatcgac    300
cgaaactgta cctcttgaac gtcttgagta catccatctc cacaaaactg ctgcattgct    360
tgaggcatca gtggttattg gggcaatctt gggaagtggc tctgatgagc agattgaaag    420
tttgcgcatg tatgcgagat catangattg ttgttccagg ttgttgatga tatacttgat    480
gtgaccaagt cttctgagga gctcggcaag acagcaggga aggacttggc gagtgacaag    540
acgacatacc cgaaattact tgggctggag aaatcacggg agtttgcaga aaagttgctt    600
tctgatgcaa gggaacaact ttcaggattt gatcaagaga ccgcagcacc acttctgcac    660
ctggccaatt atattgccta tcggcagaac tgaggtgatg ggtactccat tgattattgt    720
tgatttgtaa ctttgtaagc tcattaagat tcagatttga ggaatatctg aattatcttg    780
tgatacgtgc tagttgtagt ttcttatctt gagaagaata tctggttgac aaatgtcaat    840
ttcctaagtt agtcagtcaa acggaataat gaaaatcag cctctctgcc ctataccca    900 attgcttgat tcctgacaat tgaacacatc atatcataaa ggaagaaaat attttacctc    960
aatgttttga ttg                                                        973
```

<210> SEQ ID NO 12
<211> LENGTH: 228
<212> TYPE: PRT
<213> ORGANISM: Oryza sativa
<220> FEATURE:
<221> NAME/KEY: UNSURE
<222> LOCATION: (145)
<221> NAME/KEY: UNSURE
<222> LOCATION: (147)

<400> SEQUENCE: 12

```
His Thr Met Ser Leu Val His Asp Asp Leu Pro Cys Met Asp Asp
 1               5                  10                  15

Asp Leu Arg Arg Gly Lys Pro Thr Cys His Val Val Tyr Gly Glu Pro
             20                  25                  30

Ile Ala Val Leu Thr Gly Asp Ala Leu Leu Ser Leu Ser Phe His His
         35                  40                  45

Met Ala Arg Phe Asp Ser Tyr Pro Pro Asp Ile Asp Ala Asp Lys His
     50                  55                  60

Pro Ala Arg Val Val Arg Ala Ile Gly Glu Leu Ala Arg Cys Ile Gly
 65                  70                  75                  80

Ser Glu Gly Leu Val Ala Gly Gln Val Val Asp Leu Glu Met Thr Gly
                 85                  90                  95

Ser Thr Glu Thr Val Pro Leu Glu Arg Leu Glu Tyr Ile His Leu His
            100                 105                 110

Lys Thr Ala Ala Leu Leu Glu Ala Ser Val Val Ile Gly Ala Ile Leu
        115                 120                 125

Gly Ser Gly Ser Asp Glu Gln Ile Glu Ser Leu Arg Met Tyr Ala Arg
    130                 135                 140

Xaa Ile Xaa Leu Leu Phe Gln Val Val Asp Ile Leu Asp Val Thr
145                 150                 155                 160

Lys Ser Ser Glu Glu Leu Gly Lys Thr Ala Gly Lys Asp Leu Ala Ser
                165                 170                 175

Asp Lys Thr Thr Tyr Pro Lys Leu Leu Gly Leu Glu Lys Ser Arg Glu
            180                 185                 190

Phe Ala Glu Lys Leu Leu Ser Asp Ala Arg Glu Gln Leu Ser Gly Phe
        195                 200                 205
```

```
Asp Gln Glu Thr Ala Ala Pro Leu Leu His Leu Ala Asn Tyr Ile Ala
    210                 215                 220

Tyr Arg Gln Asn
225

<210> SEQ ID NO 13
<211> LENGTH: 973
<212> TYPE: DNA
<213> ORGANISM: Oryza sativa

<400> SEQUENCE: 13
gcacgagctt acagcacacc atgtcgctcg tccacgacga cctcccctgc atggacgacg     60
acgacctccg ccgcgggaag cccacctgcc acgtcgtcta cggggagccc atcgccgtgc    120
tcaccggcga cgcgctgctc tccctctcct tccaccacat ggccaggttc gactcctacc    180
ctccggacat cgacgctgac aagcaccccg ccgcgtcgt ccgcgccatt ggcgagctcg    240
cgcgctgcat aggctccgag ggcctagtcg ccggccaggt tgttgatctt gagatgactg    300
gctcgaccga aactgtacct cttgaacgtc ttgagtacat ccatctccac aaaactgctg    360
cattgcttga ggcatcagtg gttattgggg caatcttggg aggtggctct gatgagcaga    420
ttgaaagttt gcgcatgtat gcgagatcga taggattgtt gttccaggtt gttgatgata    480
tacttgatgt gaccaagtct tctgaggagc tcggcaagac agcagggaag gacttggcga    540
gtgacaagac gacataccg aaattacttg gctggagaa atcacgggag tttgcagaaa    600
agttgctttc tgatgcaagg gaacaacttt caggatttga tcaagagacc gcagcaccac    660
ttctgcacct ggccaattat attgcctatc ggcagaactg aggtgatggg tactccattg    720
attattgttg atttgtaact ttgtaagctc attaagattc agatttgagg aatatctgaa    780
ttatcttgtg atacgtgcta gttgtagttt cttatcttga aagaatatc tggttgacaa    840 atgtcaattt cctagttagt cagtcaaaac ggaataatga aaatcagcct ctctgcccta    900
taccccaatt gcttgattct tgacaattga acacatcata tcataaagga agaaaatatt    960
ttatcttcaa aaa                                                     973

<210> SEQ ID NO 14
<211> LENGTH: 232
<212> TYPE: PRT
<213> ORGANISM: Oryza sativa

<400> SEQUENCE: 14

Thr Ser Leu Gln His Thr Met Ser Leu Val His Asp Asp Leu Pro Cys
  1               5                  10                  15

Met Asp Asp Asp Leu Arg Arg Gly Lys Pro Thr Cys His Val Val
                 20                  25                  30

Tyr Gly Glu Pro Ile Ala Val Leu Thr Gly Asp Ala Leu Leu Ser Leu
             35                  40                  45

Ser Phe His His Met Ala Arg Phe Asp Ser Tyr Pro Pro Asp Ile Asp
         50                  55                  60

Ala Asp Lys His Pro Ala Arg Val Val Arg Ala Ile Gly Glu Leu Ala
 65                  70                  75                  80

Arg Cys Ile Gly Ser Glu Gly Leu Val Ala Gly Gln Val Val Asp Leu
                 85                  90                  95

Glu Met Thr Gly Ser Thr Glu Thr Val Pro Leu Glu Arg Leu Glu Tyr
            100                 105                 110

Ile His Leu His Lys Thr Ala Ala Leu Leu Glu Ala Ser Val Val Ile
        115                 120                 125
```

```
Gly Ala Ile Leu Gly Gly Ser Asp Glu Gln Ile Glu Ser Leu Arg
            130                 135                 140
Met Tyr Ala Arg Ser Ile Gly Leu Leu Phe Gln Val Val Asp Asp Ile
145                 150                 155                 160
Leu Asp Val Thr Lys Ser Ser Glu Glu Leu Gly Lys Thr Ala Gly Lys
                165                 170                 175
Asp Leu Ala Ser Asp Lys Thr Thr Tyr Pro Lys Leu Leu Gly Leu Glu
            180                 185                 190
Lys Ser Arg Glu Phe Ala Glu Lys Leu Leu Ser Asp Ala Arg Glu Gln
        195                 200                 205
Leu Ser Gly Phe Asp Gln Glu Thr Ala Ala Pro Leu Leu His Leu Ala
    210                 215                 220
Asn Tyr Ile Ala Tyr Arg Gln Asn
225                 230

<210> SEQ ID NO 15
<211> LENGTH: 1062
<212> TYPE: DNA
<213> ORGANISM: Glycine max
<220> FEATURE:
<221> NAME/KEY: unsure
<222> LOCATION: (411)
<221> NAME/KEY: unsure
<222> LOCATION: (998)
<221> NAME/KEY: unsure
<222> LOCATION: (1001)
<221> NAME/KEY: unsure
<222> LOCATION: (1046)

<400> SEQUENCE: 15
catgagttct ctgaatcttg gaacatggcc tcgtcccacc tctatgttga acacaccttc      60
acatctcctt cccccttttc acactctcac tctcacaaca acgcttccca aactcgcaag     120
tggaacccca aaactaatat cttcttttcc cctcgtctct gctgtgccca ctaaggaaca     180
cacagtcaca acccaggaaa ttcaactcca agacacgccg ctcaacttcg atttcaaggg     240
ctacatgatc gccaaggccc acacggtaaa ccaagccttg gacgccgcca ttgcgttgag     300
ggacccacac aagatccacc aagccatgcg ctactccctc ctcgccggcg caagagggt     360
ccgcccccgtg ctctgcatcg ccgcatgcga gctcgtcggt ggcacagagg ncaccgccat     420
ccccgccgcc tgcgccgtcg agatgatcca ccatgtcg ctcatccacg acgacctgcc     480
atgtatggac aacgacgacc tccgccgcgg aaagccgacc aaccacaagg tctacagcga     540
ggacgtggcg gtcctcgccg cgacgcgct cctcgccttc gcgttcgagc acgtggcagc     600
gtccacggag ggagtgtcgc cgtcacgcgt ggttcgagcg attggggaat tagcgaagtc     660
gatcggtacg gaagggcttg tggcgggaca agtggtggat atagattcgg aggggtggc     720
gaatgtgggg ctggagacgc tggaattcat tcacgtgcac aaaacggcgg cgttgctgga     780
actgcggttg tgttgggggc aatagtggga ggtgggagcg acgaggaggt tgagaaatta     840
aggaagttcc taggtgcatt gggttgttgt ttcaggttgt ggacgcattc tggatgttac     900
gatcgtcgga ggattgggga gacggcggga aggatttgtg ctgataggtt ctttcccagc     960
tttgggtaat agtcaaggat ttctcagatt ttaagatnca ngcatttct gcttcatctc    1020
aaagcgctcc ttgtttctta ccattnattc ttaagcaatt aa                      1062

<210> SEQ ID NO 16
<211> LENGTH: 316
<212> TYPE: PRT
```

```
<213> ORGANISM: Glycine max
<220> FEATURE:
<221> NAME/KEY: UNSURE
<222> LOCATION: (137)
<221> NAME/KEY: UNSURE
<222> LOCATION: (261)

<400> SEQUENCE: 16

Met Ser Ser Leu Asn Leu Gly Thr Trp Pro Arg Pro Thr Ser Met Leu
1               5                   10                  15

Asn Thr Pro Ser His Leu Leu Pro Pro Phe His Thr Leu Thr Leu Thr
                20                  25                  30

Thr Thr Leu Pro Lys Leu Ala Ser Gly Thr Pro Lys Leu Ile Ser Ser
            35                  40                  45

Phe Pro Leu Val Ser Ala Val Pro Thr Lys Glu His Thr Val Thr Thr
        50                  55                  60

Gln Glu Ile Gln Leu Gln Asp Thr Pro Leu Asn Phe Asp Phe Lys Gly
65                  70                  75                  80

Tyr Met Ile Ala Lys Ala His Thr Val Asn Gln Ala Leu Asp Ala Ala
                85                  90                  95

Ile Ala Leu Arg Asp Pro His Lys Ile His Gln Ala Met Arg Tyr Ser
            100                 105                 110

Leu Leu Ala Gly Gly Lys Arg Val Arg Pro Val Leu Cys Ile Ala Ala
        115                 120                 125

Cys Glu Leu Val Gly Gly Thr Glu Xaa Thr Ala Ile Pro Ala Ala Cys
130                 135                 140

Ala Val Glu Met Ile His Thr Met Ser Leu Ile His Asp Asp Leu Pro
145                 150                 155                 160

Cys Met Asp Asn Asp Asp Leu Arg Arg Gly Lys Pro Thr Asn His Lys
                165                 170                 175

Val Tyr Ser Glu Asp Val Ala Val Leu Ala Gly Asp Ala Leu Leu Ala
            180                 185                 190

Phe Ala Phe Glu His Val Ala Ala Ser Thr Glu Gly Val Ser Pro Ser
        195                 200                 205

Arg Val Val Arg Ala Ile Gly Glu Leu Ala Lys Ser Ile Gly Thr Glu
210                 215                 220

Gly Leu Val Ala Gly Gln Val Val Asp Ile Asp Ser Glu Gly Val Ala
225                 230                 235                 240

Asn Val Gly Leu Glu Thr Leu Glu Phe Ile His Val His Lys Thr Ala
                245                 250                 255

Ala Leu Leu Glu Xaa Ala Val Val Leu Gly Ala Ile Val Gly Gly Gly
            260                 265                 270

Ser Asp Glu Glu Val Glu Lys Leu Arg Lys Phe Leu Gly Ala Leu Gly
        275                 280                 285

Cys Cys Phe Arg Leu Trp Thr His Ser Gly Cys Tyr Asp Arg Arg Arg
290                 295                 300

Ile Gly Glu Thr Ala Gly Arg Ile Cys Ala Asp Arg
305                 310                 315

<210> SEQ ID NO 17
<211> LENGTH: 1268
<212> TYPE: DNA
<213> ORGANISM: Glycine max

<400> SEQUENCE: 17
gcacgagcat gagttctctg aatcttggaa catggcctcg tcccacctct atgttgaaca    60
```

-continued

```
caccttcaca tctccttccc ccttttcaca ctctcactct cacaacaacg cttcccaaac      120
tcgcaagtgg aaccccaaaa ctaatatctt cttttcccct cgtctctgct gtgcccacta      180
aggaacacac agtcacaacc caggaaattc aactccaaga cacgccgctc aacttcgatt      240
tcaagggcta catgatcgcc aaggcccaca cggtaaacca agccttggac gccgccattg      300
cgttgaggga cccacacaag atccaccaag ccatgcgcta ctccctcctc gccggcggca      360
agagggtccg ccccgtgctc tgcatcgccg catgcgagct cgtcggtggc acagaggcca      420
ccgccatccc cgccgcctgc gccgtcgaga tgatccacac catgtcgctc atccacgacg      480
acctgccatg tatggacaac gacgacctcc gccgcgaaa gccgaccaac acaaggtct       540 acggcgagga cgtggcggtc ctcgccggcg acgcgctcct cgccttcgcg ttcgagcacg      600
tggcagcgtc cacggaggga gtgtcgccgt cacgcgtggt cgagcgatt ggggaattag       660 cgaagtcgat cggtacggaa gggcttgtgg cgggacaagt ggtggatata gattcggagg      720
gggtggcgaa tgtggggctg agacgctgg aattcattca cgtgcacaaa acggcggcgt       780
tgctggaagc tgcggttgtg ttgggggcaa tagtgggagg tgggagcgac gaggaggttg      840
agaaattaag gaagttcgct aggtgcattg gttgttgtt tcaggttgtg gacgacattc       900
tggatgttac gaagtcgtcg gaggaattgg ggaagacggc ggggaaggat ttggtggctg      960
ataaggttac ttatcccaag ctattgggga tagataagtc aaaggaattt gctcaagaat     1020
tgttaaagga tgccaaggaa caattgtctg gcttcgatcc tccaaaggcg gctcccttgt     1080
ttgcattaac caattacatt gcttataggc aaaattaaaa gtgaaaacat tggataccct     1140
gttttctcac cggggaacca ctcaaataaa tttctctgct tccatttcca gtcctcaatg     1200
ctgtactgtt ctccagcgat tatttgtaat aaaataaacc tctttttttc aaaaaaaaa      1260 aaaaaaaa                                                              1268
```

<210> SEQ ID NO 18
<211> LENGTH: 369
<212> TYPE: PRT
<213> ORGANISM: Glycine max

<400> SEQUENCE: 18

```
Met Ser Ser Leu Asn Leu Gly Thr Trp Pro Arg Pro Thr Ser Met Leu
  1               5                  10                  15

Asn Thr Pro Ser His Leu Leu Pro Pro Phe His Thr Leu Thr Leu Thr
             20                  25                  30

Thr Thr Leu Pro Lys Leu Ala Ser Gly Thr Pro Lys Leu Ile Ser Ser
         35                  40                  45

Phe Pro Leu Val Ser Ala Val Pro Thr Lys Glu His Thr Val Thr Thr
     50                  55                  60

Gln Glu Ile Gln Leu Gln Asp Thr Pro Leu Asn Phe Asp Phe Lys Gly
 65                  70                  75                  80

Tyr Met Ile Ala Lys Ala His Thr Val Asn Gln Ala Leu Asp Ala Ala
                 85                  90                  95

Ile Ala Leu Arg Asp Pro His Lys Ile His Gln Ala Met Arg Tyr Ser
            100                 105                 110

Leu Leu Ala Gly Gly Lys Arg Val Arg Pro Val Leu Cys Ile Ala Ala
        115                 120                 125

Cys Glu Leu Val Gly Gly Thr Glu Ala Thr Ala Ile Pro Ala Ala Cys
    130                 135                 140

Ala Val Glu Met Ile His Thr Met Ser Leu Ile His Asp Asp Leu Pro
145                 150                 155                 160
```

```
Cys Met Asp Asn Asp Asp Leu Arg Arg Gly Lys Pro Thr Asn His Lys
                165                 170                 175
Val Tyr Gly Glu Asp Val Ala Val Leu Ala Gly Asp Ala Leu Leu Ala
            180                 185                 190
Phe Ala Phe Glu His Val Ala Ala Ser Thr Glu Gly Val Ser Pro Ser
        195                 200                 205
Arg Val Val Arg Ala Ile Gly Glu Leu Ala Lys Ser Ile Gly Thr Glu
    210                 215                 220
Gly Leu Val Ala Gly Gln Val Asp Ile Asp Ser Glu Gly Val Ala
225                 230                 235                 240
Asn Val Gly Leu Glu Thr Leu Glu Phe Ile His Val His Lys Thr Ala
                245                 250                 255
Ala Leu Leu Glu Ala Ala Val Val Leu Gly Ala Ile Val Gly Gly Gly
            260                 265                 270
Ser Asp Glu Glu Val Glu Lys Leu Arg Lys Phe Ala Arg Cys Ile Gly
        275                 280                 285
Leu Leu Phe Gln Val Val Asp Asp Ile Leu Asp Val Thr Lys Ser Ser
    290                 295                 300
Glu Glu Leu Gly Lys Thr Ala Gly Lys Asp Leu Val Ala Asp Lys Val
305                 310                 315                 320
Thr Tyr Pro Lys Leu Leu Gly Ile Asp Lys Ser Lys Glu Phe Ala Gln
                325                 330                 335
Glu Leu Leu Lys Asp Ala Lys Glu Gln Leu Ser Gly Phe Asp Pro Pro
            340                 345                 350
Lys Ala Ala Pro Leu Phe Ala Leu Thr Asn Tyr Ile Ala Tyr Arg Gln
        355                 360                 365
Asn
```

<210> SEQ ID NO 19
<211> LENGTH: 623
<212> TYPE: DNA
<213> ORGANISM: Glycine max
<220> FEATURE:
<221> NAME/KEY: unsure
<222> LOCATION: (584)

<400> SEQUENCE: 19

```
gttagtgagt gagtccaccc aaatgctggt aattcttgga ctcattggtg gaagtgtgtc      60
catgaagaac gtagtagcca gtaacaccgt aatgtctcat ctctctcact cgtgacactt     120
tcttaatccc taacccattg tcatgagtgc cctcaatttg aacgcatggc cacgccccag     180
atccagatcc agatcccgat ccccaacctt tcacgccgtc aataagttac ccttcttcac     240
cgttaccaaa cggagagcat tctcgctctc tgcggtgctc acggtcgaga cggaagagaa     300
gccaccaatc ttcgacttca agaactacat gctttccaaa gcgtccgcgg tcaacaaggc     360
cctcgacgac tccgtttcgc tccgcgagcc caagaagatc acgaggcga tgcggtactc     420
gctcctcgcc ggcggcaagc gcgtgcgccc tgtgttatgc gtggcggcgt gcgagctcgt     480
cggcgggcaa gagggcacgg cgatgcccgc cgcctgcgcc ctcgagatga tccacaccat     540
gtcgctcatc cacgacgacc tcccctgcat ggacaacgac gatntccgcc gcggcaagcc     600
caacaaccac acggtcttcg ggg                                             623
```

<210> SEQ ID NO 20
<211> LENGTH: 316
<212> TYPE: PRT

```
<213> ORGANISM: Glycine max
<220> FEATURE:
<221> NAME/KEY: UNSURE
<222> LOCATION: (137)
<221> NAME/KEY: UNSURE
<222> LOCATION: (261)

<400> SEQUENCE: 20
```

Met Ser Ser Leu Asn Leu Gly Thr Trp Pro Arg Pro Thr Ser Met Leu
 1               5                  10                  15

Asn Thr Pro Ser His Leu Leu Pro Pro Phe His Thr Leu Thr Leu Thr
                20                  25                  30

Thr Thr Leu Pro Lys Leu Ala Ser Gly Thr Pro Lys Leu Ile Ser Ser
            35                  40                  45

Phe Pro Leu Val Ser Ala Val Pro Thr Lys Glu His Thr Val Thr Thr
        50                  55                  60

Gln Glu Ile Gln Leu Gln Asp Thr Pro Leu Asn Phe Asp Phe Lys Gly
 65                  70                  75                  80

Tyr Met Ile Ala Lys Ala His Thr Val Asn Gln Ala Leu Asp Ala Ala
                85                  90                  95

Ile Ala Leu Arg Asp Pro His Lys Ile His Gln Ala Met Arg Tyr Ser
            100                 105                 110

Leu Leu Ala Gly Gly Lys Arg Val Arg Pro Val Leu Cys Ile Ala Ala
        115                 120                 125

Cys Glu Leu Val Gly Gly Thr Glu Xaa Thr Ala Ile Pro Ala Ala Cys
130                 135                 140

Ala Val Glu Met Ile His Thr Met Ser Leu Ile His Asp Asp Leu Pro
145                 150                 155                 160

Cys Met Asp Asn Asp Asp Leu Arg Arg Gly Lys Pro Thr Asn His Lys
                165                 170                 175

Val Tyr Ser Glu Asp Val Ala Val Leu Ala Gly Asp Ala Leu Leu Ala
            180                 185                 190

Phe Ala Phe Glu His Val Ala Ala Ser Thr Glu Gly Val Ser Pro Ser
        195                 200                 205

Arg Val Val Arg Ala Ile Gly Glu Leu Ala Lys Ser Ile Gly Thr Glu
    210                 215                 220

Gly Leu Val Ala Gly Gln Val Val Asp Ile Asp Ser Glu Gly Val Ala
225                 230                 235                 240

Asn Val Gly Leu Glu Thr Leu Glu Phe Ile His Val His Lys Thr Ala
                245                 250                 255

Ala Leu Leu Glu Xaa Ala Val Val Leu Gly Ala Ile Val Gly Gly Gly
            260                 265                 270

Ser Asp Glu Glu Val Glu Lys Leu Arg Lys Phe Leu Gly Ala Leu Gly
        275                 280                 285

Cys Cys Phe Arg Leu Trp Thr His Ser Gly Cys Tyr Asp Arg Arg Arg
    290                 295                 300

Ile Gly Glu Thr Ala Gly Arg Ile Cys Ala Asp Arg
305                 310                 315

```
<210> SEQ ID NO 21
<211> LENGTH: 1441
<212> TYPE: DNA
<213> ORGANISM: Glycine max

<400> SEQUENCE: 21
gcacgaggtt agtgagtgag tccacccaaa tgctggtaat tcttggactc attggtggaa    60
```

-continued

| | |
|---|---|
| gtgtgtccat gaagaacgta gtagccagta acaccgtaat gtctcatctc tctcactcgt | 120 |
| gacactttct taatccctaa cccattgtca tgagtgccct caatttgaac gcatggccac | 180 |
| gccccagatc cagatccaga tcccgatccc caacctttca cgccgtcaat aagttaccct | 240 |
| tcttcaccgt taccaaacgg agagcattct cgctctctgc ggtgctcacg gtcgagacgg | 300 |
| aagagaagcc accaatcttc gacttcaaga actacatgct ttccaaagcg tccgcggtca | 360 |
| acaagggcct cgacgactcc gtttcgctcc gcgagcccaa gaagatccac gaggcgatgc | 420 |
| ggtactcgct cctcgccggc ggcaagcgcg tgcgccctgt gttatgcgtg cggcgtgcg | 480 |
| agctcgtcgg cgggcacgag gccacggcga tgcccgccgc ctgcgccctc gagatgatcc | 540 |
| acaccatgtc gctcatccac gacgacctcc cctgcatgga caacgacgat ctccgccgcg | 600 |
| gcaagcccac caaccacacg gtcttcggcg aggacgtcgc cgtcctcgcc ggcgacgccc | 660 |
| tcctggcctt cgccttcgag cacatcgccg cctccacccg ggggcctcg gcgccccgga | 720 |
| tcctccgcgc gatcggcgag ctcgcgcggt cgatcggctc cgaggcctc gttgccggcc | 780 |
| aggtcgtcga catcaactct gagggcctgg ccgacgttgg cctagagcgc ctggagttca | 840 |
| tccacgtcca caagaccgcc gcgctcctcg agggtgcggt tgtcctcggc gccatcctcg | 900 |
| gcggcggcac cgacgacgag gtcgaaaaat tgagaaaatt cgctcgctac attggtctac | 960 |
| tctttcaggt tgttgatgac attctcgatg ttactaagtc ttcccaggaa ttgggaaaga | 1020 |
| ccgctggaaa agaccttgtg gctgataagg ttacttaccc caagcttttg gggattgaga | 1080 |
| agtctaagga gtttgctgcg aaactgaaca aggatgctca ggatcagctt gctggctttg | 1140 |
| accctgttaa ggctgctcct ttgattgctt tagccaatta cattgcttat aggcagaact | 1200 |
| agattattgt tcttgtctct actttacaaa caaatcattg tttgttttag gaatatttag | 1260 |
| tttttttatga aatgaaaatc attggattta catttattta catattgcaa tgcaactagg | 1320 |
| gattattaaa taggagcctc ccctgccctt cttctatgtg cctgccatag tcgtcaattt | 1380 |
| tgtatgatga ataactataa atattagaat acctttaatt tgtaaaaaaa aaaaaaaaa | 1440 |
| a | 1441 |

<210> SEQ ID NO 22
<211> LENGTH: 350
<212> TYPE: PRT
<213> ORGANISM: Glycine max

<400> SEQUENCE: 22

Met Ser Ala Leu Asn Leu Asn Ala Trp Pro Arg Pro Arg Ser Arg Ser
 1               5                  10                  15

Arg Ser Arg Ser Pro Thr Phe His Ala Val Asn Lys Leu Pro Phe Phe
            20                  25                  30

Thr Val Thr Lys Arg Arg Ala Phe Ser Leu Ser Ala Val Leu Thr Val
        35                  40                  45

Glu Thr Glu Glu Lys Pro Pro Ile Phe Asp Phe Lys Asn Tyr Met Leu
    50                  55                  60

Ser Lys Ala Ser Ala Val Asn Lys Gly Leu Asp Asp Ser Val Ser Leu
65                  70                  75                  80

Arg Glu Pro Lys Lys Ile His Glu Ala Met Arg Tyr Ser Leu Leu Ala
                85                  90                  95

Gly Gly Lys Arg Val Arg Pro Val Leu Cys Val Ala Ala Cys Glu Leu
            100                 105                 110

Val Gly Gly His Glu Ala Thr Ala Met Pro Ala Ala Cys Ala Leu Glu
        115                 120                 125

```
Met Ile His Thr Met Ser Leu Ile His Asp Asp Leu Pro Cys Met Asp
        130                 135                 140

Asn Asp Asp Leu Arg Arg Gly Lys Pro Thr Asn His Thr Val Phe Gly
145                 150                 155                 160

Glu Asp Val Ala Val Leu Ala Gly Asp Ala Leu Leu Ala Phe Ala Phe
                165                 170                 175

Glu His Ile Ala Ala Ser Thr Arg Gly Ala Ser Ala Pro Arg Ile Leu
            180                 185                 190

Arg Ala Ile Gly Glu Leu Ala Arg Ser Ile Gly Ser Glu Gly Leu Val
        195                 200                 205

Ala Gly Gln Val Val Asp Ile Asn Ser Glu Gly Leu Ala Asp Val Gly
210                 215                 220

Leu Glu Arg Leu Glu Phe Ile His Val His Lys Thr Ala Ala Leu Leu
225                 230                 235                 240

Glu Gly Ala Val Val Leu Gly Ala Ile Leu Gly Gly Gly Thr Asp Asp
                245                 250                 255

Glu Val Glu Lys Leu Arg Lys Phe Ala Arg Tyr Ile Gly Leu Leu Phe
            260                 265                 270

Gln Val Val Asp Asp Ile Leu Asp Val Thr Lys Ser Ser Gln Glu Leu
        275                 280                 285

Gly Lys Thr Ala Gly Lys Asp Leu Val Ala Asp Lys Val Thr Tyr Pro
    290                 295                 300

Lys Leu Leu Gly Ile Glu Lys Ser Lys Glu Phe Ala Ala Lys Leu Asn
305                 310                 315                 320

Lys Asp Ala Gln Asp Gln Leu Ala Gly Phe Asp Pro Val Lys Ala Ala
                325                 330                 335

Pro Leu Ile Ala Leu Ala Asn Tyr Ile Ala Tyr Arg Gln Asn
            340                 345                 350

<210> SEQ ID NO 23
<211> LENGTH: 993
<212> TYPE: DNA
<213> ORGANISM: Glycine max
<220> FEATURE:
<221> NAME/KEY: unsure
<222> LOCATION: (882)
<221> NAME/KEY: unsure
<222> LOCATION: (949)
<221> NAME/KEY: unsure
<222> LOCATION: (952)
<221> NAME/KEY: unsure
<222> LOCATION: (977)
<221> NAME/KEY: unsure
<222> LOCATION: (979)

<400> SEQUENCE: 23
gcgttgtgtt gtgtcctgtg ctagttgaat ctcatctaac cccaaatact aagatcctat      60
cctactactc atttgcttat ccatcatcaa caactctcat ttctcatcat cacttcccac     120
ttacgctcgg taatgtctca tttctcacgc atcaacccct aataataatc ccccaaacag     180
aacctttccc acccaatcca aacacagccc taaaccccCC caccatcatc atgagtgccg     240
tgaatttgaa cacatggcca cgccccagct tcattttgaa ccaaaccgcc acaagaagat     300
ccagatcctc cccaacctct catttctttc acggcgtcaa taagttaccg tcacccattt     360
cctccctcac cgttgccaaa cgctcattta cgctctcggc ggtgctgacg aaagaggaca     420
ccgtggagac ggaagagaag ccaccgattt tcgacttcaa gaactacatg gtttccaaag     480
cgagcgcggt gaacaaggcc ctcgacgacg ccgtttcgct ccgcgagccg cagaagatcc     540
```

```
acgaggcgat gcggtactcg ctcctcgccg gcggcaagcg cgtgaggccg gttttgtgcg      600
tggcggcctg cgagctcgtc ggcggcgagg aggccacggc gatgcccgcc gcctgcgcca      660
tcgagatgat ccacaccatg tcgctcatcc acgatgacct ccctgcatg gacaacgacg       720 acctccgccg cggtaagccc acaacacaag tcttcggcga ggactcgcgt ctcgcggcga      780
ccgctctcgc ttcgccttcg agcacatcgc cgctcaaccg gggcgctccc cggggcgatc      840
gtccgcgcga tcggcgagct tgcgcggtcg atcggctccg anggactttg tcgccggcca      900
ggtcgtcgac atcaactccc gaagggcctg gccgacgttg gacctcganc gnctccgagt      960
tcatccaacg tcaacangng gggacaacga cga                                    993
```

\<210\> SEQ ID NO 24
\<211\> LENGTH: 171
\<212\> TYPE: PRT
\<213\> ORGANISM: Glycine max

\<400\> SEQUENCE: 24

```
Met Ser Ala Val Asn Leu Asn Thr Trp Pro Arg Pro Ser Phe Ile Leu
  1               5                  10                  15

Asn Gln Thr Ala Thr Arg Arg Ser Arg Ser Ser Pro Thr Ser His Phe
             20                  25                  30

Phe His Gly Val Asn Lys Leu Pro Ser Pro Ile Ser Ser Leu Thr Val
         35                  40                  45

Ala Lys Arg Ser Phe Thr Leu Ser Ala Val Leu Thr Lys Glu Asp Thr
     50                  55                  60

Val Glu Thr Glu Glu Lys Pro Pro Ile Phe Asp Phe Lys Asn Tyr Met
 65                  70                  75                  80

Val Ser Lys Ala Ser Ala Val Asn Lys Ala Leu Asp Asp Ala Val Ser
                 85                  90                  95

Leu Arg Glu Pro Gln Lys Ile His Glu Ala Met Arg Tyr Ser Leu Leu
            100                 105                 110

Ala Gly Gly Lys Arg Val Arg Pro Val Leu Cys Val Ala Ala Cys Glu
        115                 120                 125

Leu Val Gly Gly Glu Glu Ala Thr Ala Met Pro Ala Ala Cys Ala Ile
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr
                165                 170
```

\<210\> SEQ ID NO 25
\<211\> LENGTH: 1470
\<212\> TYPE: DNA
\<213\> ORGANISM: Glycine max

\<400\> SEQUENCE: 25

```
gcacgaggcg ttgtgttgtg tcctgtgcta gttgaatctc atctaacccc aaatactaag       60
atcctatcct actactcatt tgcttatcca tcatcaacaa ctctcatttc tcatcatcac      120
ttcccactta cgctcggtaa tgtctcattt ctcacgcatc aaccctaat aataatcccc       180 caaacagaac ctttcccacc caatccaaac acagccctaa accccccac catcatcatg       240 agtgccgtga atttgaacac atggccacgc ccagcttca ttttgaacca aaccgccaca       300
agaagatcca gatcctcccc aacctctcat ttctttcacg gcgtcaataa gttaccgtca      360
cccatttcct ccctcaccgt tgccaaacgc tcatttacgc tctcggcggt gctgacgaaa      420
```

```
gaggacaccg tggagacgga agagaagcca ccgattttcg acttcaagaa ctacatggtt      480
tccaaagcga gcgcggtgaa caaggccctc gacgacgccg tttcgctccg cgagccgcag      540
aagatccacg aggcgatgcg gtactcgctc ctcgccggcg gcaagcgcgt gaggccggtt      600
ttgtgcgtgg cggcctgcga gctcgtcggc ggcgaggagg ccacggcgat gcccgccgcc      660
tgcgccatcg agatgatcca caccatgtcg ctcatccacg atgacctccc ctgcatggac      720
aacgacgacc tccgccgcgg taagcccacc aaccacaagg tcttcggcga ggacgtcgcc      780
gtcctcgccg gcgacgcgct cctcgccttc gccttcgagc acatcgccgc tccaccccgg      840
ggcgcctccc cggggcggat cgtccgcgcg atcggcgagc ttgcgcggtc gatcggctcc      900
gagggacttg tcgccggcca ggtcgtcgac atcaactccg agggcctggc cgacgtggac      960
ctcgagcgcc tcgagttcat ccacgtccac aagactgccg cgctcctcga gggtgcggtg     1020
gtgctcggcg ccatcctcgg cggcggcacc gacgacgagg tcgagaaatt gagaaaattc     1080
gctcgctaca ttggtctgct ctttcaggtt gttgatgaca ttctcgatgt taccaagtca     1140
tctcaggaat tggggaaaac cgcaggaaaa gaccttgtgg cagataaggt tacttacccc     1200
aaacttttgg gtattgagaa atctaaggtg tttgctgcga gttgaacaa agatgctcag      1260 gatcagcttg ttgggtttga ccctgttaag gctgctcctt tgattgcttt agccaattac     1320
attgcttata ggcagaacta gattgtttgt ttaggaaagt ttagatttat gaaatcatat     1380
tggattaaca tttacttatt ggctattgca atgcaactag ggattataaa ataataatac     1440
ccccttgccc ttaaaaaaaa aaaaaaaaaa                                     1470
```

<210> SEQ ID NO 26
<211> LENGTH: 367
<212> TYPE: PRT
<213> ORGANISM: Glycine max

<400> SEQUENCE: 26

```
Met Ser Ala Val Asn Leu Asn Thr Trp Pro Arg Pro Ser Phe Ile Leu
  1               5                  10                  15

Asn Gln Thr Ala Thr Arg Arg Ser Arg Ser Ser Pro Thr Ser His Phe
             20                  25                  30

Phe His Gly Val Asn Lys Leu Pro Ser Pro Ile Ser Ser Leu Thr Val
         35                  40                  45

Ala Lys Arg Ser Phe Thr Leu Ser Ala Val Leu Thr Lys Glu Asp Thr
     50                  55                  60

Val Glu Thr Glu Glu Lys Pro Pro Ile Phe Asp Phe Lys Asn Tyr Met
 65                  70                  75                  80

Val Ser Lys Ala Ser Ala Val Asn Lys Ala Leu Asp Asp Ala Val Ser
                 85                  90                  95

Leu Arg Glu Pro Gln Lys Ile His Glu Ala Met Arg Tyr Ser Leu Leu
            100                 105                 110

Ala Gly Gly Lys Arg Val Arg Pro Val Leu Cys Val Ala Ala Cys Glu
        115                 120                 125

Leu Val Gly Gly Glu Glu Ala Thr Ala Met Pro Ala Ala Cys Ala Ile
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ala Phe Ala
```

```
              180                 185                 190
Phe Glu His Ile Ala Ala Ser Thr Arg Gly Ala Ser Pro Gly Arg Ile
        195                 200                 205
Val Arg Ala Ile Gly Glu Leu Ala Arg Ser Ile Gly Ser Glu Gly Leu
    210                 215                 220
Val Ala Gly Gln Val Val Asp Ile Asn Ser Glu Gly Leu Ala Asp Val
225                 230                 235                 240
Asp Leu Glu Arg Leu Glu Phe Ile His Val His Lys Thr Ala Leu
                245                 250                 255
Leu Glu Gly Ala Val Val Leu Gly Ala Ile Leu Gly Gly Gly Thr Asp
            260                 265                 270
Asp Glu Val Glu Lys Leu Arg Lys Phe Ala Arg Tyr Ile Gly Leu Leu
        275                 280                 285
Phe Gln Val Val Asp Asp Ile Leu Asp Val Thr Lys Ser Ser Gln Glu
    290                 295                 300
Leu Gly Lys Thr Ala Gly Lys Asp Leu Val Asp Lys Val Thr Tyr
305                 310                 315                 320
Pro Lys Leu Leu Gly Ile Glu Lys Ser Lys Val Phe Ala Ala Lys Leu
                325                 330                 335
Asn Lys Asp Ala Gln Asp Gln Leu Val Gly Phe Asp Pro Val Lys Ala
            340                 345                 350
Ala Pro Leu Ile Ala Leu Ala Asn Tyr Ile Ala Tyr Arg Gln Asn
        355                 360                 365

<210> SEQ ID NO 27
<211> LENGTH: 582
<212> TYPE: DNA
<213> ORGANISM: Triticum aestivum
<220> FEATURE:
<221> NAME/KEY: unsure
<222> LOCATION: (477)
<221> NAME/KEY: unsure
<222> LOCATION: (488)..(489)
<221> NAME/KEY: unsure
<222> LOCATION: (529)
<221> NAME/KEY: unsure
<222> LOCATION: (550)
<221> NAME/KEY: unsure
<222> LOCATION: (580)

<400> SEQUENCE: 27
gttgttgatc tggagatgac tggctcaact gagactgttc cacttgaccg ccttgagtac     60
atccatctgc acaagactgc tgcattgctt gaggcctcag tggttattgg agcaatcatc    120
gggggtggct cggaagagca gattgagcgg ttgcgcaagt acgcgagatc aattgggctg    180
ctgttccagg tggttgatga cattcttgat gtgaccaagt catcagagga gctagggaag    240
acagctggga aggacttggc gagtgacaag acgacatacc cgaagttact agggttggag    300
aagtcacagg aatttgcgga gaagttgctt tctgatgcaa aggagcaact tgctgatttt    360
gataaagaga aggcagcacc gctattgtac ttggcaatta tattgcctat ccggcagaac    420
taaggtgatg gtatcctgtt gtttgttgtt tatccgtaac tttggtaaga acacaanccg    480
gggatttnna ggaatatctg aatcctcccc tcaatatata ctatttaant tcctaccgt    540 tggtgtcaan gagaatatta aggtgacaaa accacatgan tg                       582

<210> SEQ ID NO 28
<211> LENGTH: 128
<212> TYPE: PRT
<213> ORGANISM: Triticum aestivum
```

```
<400> SEQUENCE: 28

Val Pro Leu Asp Arg Leu Glu Tyr Ile His Leu His Lys Thr Ala Ala
 1               5                  10                  15

Leu Leu Glu Ala Ser Val Val Ile Gly Ala Ile Gly Gly Ser
             20                  25                  30

Glu Glu Gln Ile Glu Arg Leu Arg Lys Tyr Ala Arg Ser Ile Gly Leu
             35                  40                  45

Leu Phe Gln Val Val Asp Asp Ile Leu Asp Val Thr Lys Ser Ser Glu
             50                  55                  60

Glu Leu Gly Lys Thr Ala Gly Lys Asp Leu Ala Ser Asp Lys Thr Thr
65                  70                  75                  80

Tyr Pro Lys Leu Leu Gly Leu Glu Lys Ser Gln Glu Phe Ala Glu Lys
                 85                  90                  95

Leu Leu Ser Asp Ala Lys Glu Gln Leu Ala Asp Phe Asp Lys Glu Lys
                100                 105                 110

Ala Ala Pro Leu Leu Tyr Leu Ala Ile Ile Leu Pro Ile Arg Gln Asn
            115                 120                 125
```

<210> SEQ ID NO 29
<211> LENGTH: 859
<212> TYPE: DNA
<213> ORGANISM: Triticum aestivum

<400> SEQUENCE: 29

```
gccgcggcaa ggccacctgc acgtcgtgt  acgcgagcc  catcgccgtg  ctcgccggcg     60
acgccctgct cgcgctcgcc ttcgagcaca tggccagcct cgactcctac cccccggacg    120
tcgaccccgc caagcacacc gcccgcgtcg tccgcgccat ggtgagctc  gcgcgctgca    180
tcggttcaga gggcctcgtc gccggccagg ttgttgatct ggagatgact ggctcaactg    240
agactgttcc acttgaccgc cttgagtaca tccatctgca caagactgct gcattgcttg    300
aggcctcagt ggttattgga gcaatcatcg ggggtggctc ggaagagcag attgagcggt    360
tgcgcaagta cgcgagatca attgggctgc tgttccaggt ggttgatgac attcttgatg    420
tgaccaagtc atcagaggag ctagggaaga cagctgggaa ggacttggcg agtgacaaga    480
cgacataccc gaagttacta gggttggaga agtcacagga atttgcggag aagttgcttt    540
ctgatgcaaa ggagcaactt gctgattttg ataaagagaa ggcagcaccg ctattgtact    600
tggccaatta tattgcctat cggcagaact aaggtgatgg ttattctgtt gtttgttgtt    660
tatctgtaac tttgtaagaa catcaagtct gggatttgag gaatatctga attcttcccc    720
tcatatatac tagtttagtt ttctaccgtt gtgtcatgag aatatttagg tgacaaaagc    780
cacatgagtt aggtggcaaa taccaatgtc ccattgagat agccaagaca ttataatggg    840
aatcagcctt tatgtctaa                                                 859
```

<210> SEQ ID NO 30
<211> LENGTH: 209
<212> TYPE: PRT
<213> ORGANISM: Triticum aestivum

<400> SEQUENCE: 30

```
Arg Gly Lys Ala Thr Cys His Val Val Tyr Gly Glu Pro Ile Ala Val
 1               5                  10                  15

Leu Ala Gly Asp Ala Leu Leu Ala Leu Ala Phe Glu His Met Ala Ser
             20                  25                  30
```

```
Leu Asp Ser Tyr Pro Pro Asp Val Asp Pro Ala Lys His Thr Ala Arg
         35                  40                  45

Val Val Arg Ala Ile Gly Glu Leu Ala Arg Cys Ile Gly Ser Glu Gly
 50                  55                  60

Leu Val Ala Gly Gln Val Val Asp Leu Glu Met Thr Gly Ser Thr Glu
 65                  70                  75                  80

Thr Val Pro Leu Asp Arg Leu Glu Tyr Ile His Leu His Lys Thr Ala
                 85                  90                  95

Ala Leu Leu Glu Ala Ser Val Val Ile Gly Ala Ile Gly Gly Gly
                100                 105                 110

Ser Glu Glu Gln Ile Glu Arg Leu Arg Lys Tyr Ala Arg Ser Ile Gly
            115                 120                 125

Leu Leu Phe Gln Val Val Asp Asp Ile Leu Asp Val Thr Lys Ser Ser
130                 135                 140

Glu Glu Leu Gly Lys Thr Ala Gly Lys Asp Leu Ala Ser Asp Lys Thr
145                 150                 155                 160

Thr Tyr Pro Lys Leu Leu Gly Leu Glu Lys Ser Gln Glu Phe Ala Glu
                165                 170                 175

Lys Leu Leu Ser Asp Ala Lys Glu Gln Leu Ala Asp Phe Asp Lys Glu
            180                 185                 190

Lys Ala Ala Pro Leu Leu Tyr Leu Ala Asn Tyr Ile Ala Tyr Arg Gln
        195                 200                 205

Asn
```

```
<210> SEQ ID NO 31
<211> LENGTH: 556
<212> TYPE: DNA
<213> ORGANISM: Oryza sativa
<220> FEATURE:
<221> NAME/KEY: unsure
<222> LOCATION: (424)
<221> NAME/KEY: unsure
<222> LOCATION: (499)
<221> NAME/KEY: unsure
<222> LOCATION: (535)
<221> NAME/KEY: unsure
<222> LOCATION: (554)

<400> SEQUENCE: 31
cttacagttg tgaaccccca attccaatct cccccttttca tcagcgccat ggctctctcc      60
tccttctcca tgtccctccc cttcgccaag ctgccttcca cctccaaatc cacccgcttc     120
cttcccatcc gggcctcctc tgccgccgcc gccgcctccc cttccttcga tttgcgcctc     180
tattggacat ccctgatcgc cgatgtggag gccgagctcg acgccgcgat gcccatccgc     240
acgccggaga gaatccactc cgccatgcgc tacgccgtcc tcccgggcgc cggcaacgag     300
ggcaccgcca agcgcgcgcc cccggtcctc tgcgtcgccg cctgcgagct cctcggcgcg     360
cgcgcgaagg ccgcgctccc cgccgctgtg gccctcgaga tgctccacgc gggcgtcgct     420
cgtngcacga cgacctccat ggcttcgaag gccgcggccc aacccgccgg cggggggccc     480
tcaacccaag gccgcctang gaaccgaac atgggcgttc ccgcccggg ggaagggct        540 ccttcccct cggnca                                                      556
```

```
<210> SEQ ID NO 32
<211> LENGTH: 123
<212> TYPE: PRT
<213> ORGANISM: Oryza sativa

<400> SEQUENCE: 32
```

```
Ser Ala Met Ala Leu Ser Ser Phe Ser Met Ser Leu Pro Phe Ala Lys
 1               5                  10                  15

Leu Pro Ser Thr Ser Lys Ser Thr Arg Phe Leu Pro Ile Arg Ala Ser
             20                  25                  30

Ser Ala Ala Ala Ala Ser Pro Ser Phe Asp Leu Arg Leu Tyr Trp
         35                  40                  45

Thr Ser Leu Ile Ala Asp Val Glu Ala Glu Leu Asp Ala Ala Met Pro
     50                  55                  60

Ile Arg Thr Pro Glu Arg Ile His Ser Ala Met Arg Tyr Ala Val Leu
 65                  70                  75                  80

Pro Gly Ala Gly Asn Glu Gly Thr Ala Lys Arg Ala Pro Pro Val Leu
                 85                  90                  95

Cys Val Ala Ala Cys Glu Leu Leu Gly Ala Arg Ala Lys Ala Ala Leu
                100                 105                 110

Pro Ala Ala Val Ala Leu Glu Met Leu His Ala
            115                 120
```

<210> SEQ ID NO 33
<211> LENGTH: 1428
<212> TYPE: DNA
<213> ORGANISM: Oryza sativa

<400> SEQUENCE: 33

```
gcacgagctt acagttgtga accccccaatc caattccaat ctccccttt catcagcgcc      60
atggctctct cctccttctc catgtccctc cccttcgcca agctgccttc cacctccaaa     120
tccacccgct tccttcccat ccgggcctcc tctgccgccg ccgccgcctc cccttccttc     180
gatttgcgcc tctattggac atccctgatc gccgatgtgg aggccgagct cgacgccgcg     240
atgcccatcc gcacgccgga gagaatccac tccgccatgc gctacgccgt cctcccgggc     300
gccggcaacg agggcaccgc caagcgcgcg ccccgggtcc tctgcgtcgc cgcctgcgag     360
ctcctcggcg cgcgcgcga ggccgcgctc ccgccgctg tggccctcga gatgctccac     420
gcggcgtcgc tcgtgcacga cgacctccca tgcttcgacg ccgcgccac ccgccgcggg     480
cgcccctcca cccacgccgc ctacggcacc gacatggccg tcctcgccgg ggacgcgctc     540
ttccccctcg cctacaccca cgtcatcgcc cacactccgt cgcccgaccc cgtaccccac     600
gccgtcctcc tccgcgtcct cggggagcta gcgcgcgccg tgggatccac aggcatggcg     660
gccggccaat tcctcgacct cgccggcgcc accgccctcg cgcaggccga ggtcatgaag     720
gttctgacga agaagttcgg cgagatggcg gagtgctccg ccgcctgcgg cgccatgctg     780
ggaggcgcgg ggcccgacga ggaggccgcg ctgcggcgct acggccgcac catccggcgtc    840
ctgtaccagc tcgtcgacga catccggagc gcgtcgggca acggcaagat gaggagcaat     900
gccagcgtcc tgcgcgcgct gggcatggat cgagcgctcg gcatcgtaga ggagctcaaa     960
gcgcaggcca agatggaggc cgacaggttc ggtgacaagt atggcaaaag ggtgcttccc    1020
ttgtacagct tcgtggacta tgcggtggag aggggattcg agctgcagga tgcagctaca    1080
acgccgtagg cacggaccgc gcagaccaac cttgatgcta ccggatattt gaagttctga    1140
gcaagtggtt atatatggag ttatatgctg ctgagatttg gtgagcaatt catctctgaa    1200
attataagtt tcaatgagaa atataaagat tacgccattg ccatctaggg cagatgtctg    1260
gatacttatg ctgcggttct gatctttagt tagttgctga ataagacga tgtgactaaa    1320
tgaagaattc ttaggataaa ctaccacaat tgctatgcct tggtgttaca tgtgcttaat    1380
```

```
atatataatc tgatcacaat ttcaaagcca aaaaaaaaaa aaaaaaa        1428
```

<210> SEQ ID NO 34
<211> LENGTH: 342
<212> TYPE: PRT
<213> ORGANISM: Oryza sativa

<400> SEQUENCE: 34

```
Met Ala Leu Ser Ser Phe Ser Met Ser Leu Pro Phe Ala Lys Leu Pro
 1               5                  10                  15

Ser Thr Ser Lys Ser Thr Arg Phe Leu Pro Ile Arg Ala Ser Ser Ala
            20                  25                  30

Ala Ala Ala Ser Pro Ser Phe Asp Leu Arg Leu Tyr Trp Thr Ser
        35                  40                  45

Leu Ile Ala Asp Val Glu Ala Glu Leu Asp Ala Ala Met Pro Ile Arg
    50                  55                  60

Thr Pro Glu Arg Ile His Ser Ala Met Arg Tyr Ala Val Leu Pro Gly
65                  70                  75                  80

Ala Gly Asn Glu Gly Thr Ala Lys Arg Ala Pro Val Leu Cys Val
                85                  90                  95

Ala Ala Cys Glu Leu Leu Gly Ala Pro Arg Glu Ala Ala Leu Pro Ala
            100                 105                 110

Ala Val Ala Leu Glu Met Leu His Ala Ala Ser Leu Val His Asp Asp
        115                 120                 125

Leu Pro Cys Phe Asp Ala Ala Pro Thr Arg Arg Gly Arg Pro Ser Thr
    130                 135                 140

His Ala Ala Tyr Gly Thr Asp Met Ala Val Leu Ala Gly Asp Ala Leu
145                 150                 155                 160

Phe Pro Leu Ala Tyr Thr His Val Ile Ala His Thr Pro Ser Pro Asp
                165                 170                 175

Pro Val Pro His Ala Val Leu Leu Arg Val Leu Gly Glu Leu Ala Arg
            180                 185                 190

Ala Val Gly Ser Thr Gly Met Ala Ala Gly Gln Phe Leu Asp Leu Ala
        195                 200                 205

Gly Ala Thr Ala Leu Gly Glu Ala Glu Val Met Lys Val Leu Thr Lys
    210                 215                 220

Lys Phe Gly Glu Met Ala Glu Cys Ser Ala Ala Cys Gly Ala Met Leu
225                 230                 235                 240

Gly Gly Ala Gly Pro Asp Glu Glu Ala Ala Leu Arg Arg Tyr Gly Arg
                245                 250                 255

Thr Ile Gly Val Leu Tyr Gln Leu Val Asp Asp Ile Arg Ser Ala Ser
            260                 265                 270

Gly Asn Gly Lys Met Arg Ser Asn Ala Ser Val Leu Arg Ala Leu Gly
        275                 280                 285

Met Asp Arg Ala Leu Gly Ile Val Glu Glu Leu Lys Ala Gln Ala Lys
    290                 295                 300

Met Glu Ala Asp Arg Phe Gly Asp Lys Tyr Gly Glu Arg Val Leu Pro
305                 310                 315                 320

Leu Tyr Ser Phe Val Asp Tyr Ala Val Glu Arg Gly Phe Glu Leu Gln
                325                 330                 335

Asp Ala Ala Thr Thr Pro
            340
```

<210> SEQ ID NO 35
<211> LENGTH: 538

```
<212> TYPE: DNA
<213> ORGANISM: Glycine max
<220> FEATURE:
<221> NAME/KEY: unsure
<222> LOCATION: (496)
<221> NAME/KEY: unsure
<222> LOCATION: (507)
<221> NAME/KEY: unsure
<222> LOCATION: (523)
<221> NAME/KEY: unsure
<222> LOCATION: (530)
<221> NAME/KEY: unsure
<222> LOCATION: (533)

<400> SEQUENCE: 35
ccataacctt atctatcgca accacctccc aaatcactct catccaactt catctctctc      60
ttcccccagt tgccagatct gaatcacacc ttcactcttg cgatttaatt actgagtagt     120
tgaggatggc tccttttgct tttgcaacat tgccctcttc tcacatctgc cgcctcccaa     180
agcccacaaa cttgaagttt cgagttcgct gctctactgc cgcgtcttct ccttcttcgg     240
tttccactag atcaaaagct gctggctttg atttgaagac atactgggcc aacctaatgg     300
tgcagatcaa tcagaagctg gacgaagcta cccggttca gtttcctccg cagatatatg      360
aagctatgag gtattcagtc cttgccaaag gtgccaagcg agccccacct gttatgtgca     420
tctctgcctg tgaactcttt ggtggaagcc gccttgccgg cttccccaat gcctggtgcc     480
cttgaaatgg gtcaangaag cttcaantga tacacgatga ttntccctgn atnggtga      538

<210> SEQ ID NO 36
<211> LENGTH: 116
<212> TYPE: PRT
<213> ORGANISM: Glycine max

<400> SEQUENCE: 36

Phe Ala Phe Ala Thr Leu Pro Ser Ser His Ile Cys Arg Leu Pro Lys
  1               5                  10                  15

Pro Thr Asn Leu Lys Phe Arg Val Arg Cys Ser Thr Ala Ala Ser Ser
             20                  25                  30

Pro Ser Ser Val Ser Thr Arg Ser Lys Ala Ala Gly Phe Asp Leu Lys
         35                  40                  45

Thr Tyr Trp Ala Asn Leu Met Val Gln Ile Asn Gln Lys Leu Asp Glu
     50                  55                  60

Ala Ile Pro Val Gln Phe Pro Pro Gln Ile Tyr Glu Ala Met Arg Tyr
 65                  70                  75                  80

Ser Val Leu Ala Lys Gly Ala Lys Arg Ala Pro Pro Val Met Cys Ile
                 85                  90                  95

Ser Ala Cys Glu Leu Phe Gly Gly Ser Arg Leu Ala Gly Phe Pro Asn
            100                 105                 110

Ala Trp Cys Pro
        115

<210> SEQ ID NO 37
<211> LENGTH: 1161
<212> TYPE: DNA
<213> ORGANISM: Glycine max

<400> SEQUENCE: 37
gcacgagcca taaccttatc tatcgcaacc acctcccaaa tcactctcat ccaacttcat      60
ctctctcttc cccagttgc cagatctgaa tcacacttc actcttgcga tttaattact      120
gagtagttga ggatggctcc ttttgctttt gcaacattgc cctcttctca catctgccgc     180
```

-continued

```
ctcccaaagc ccacaaactt gaagtttcga gttcgctgct ctactgccgc gtcttctcct        240
tcttcggttt ccactagatc aaaagctgct ggctttgatt tgaagacata ctgggccaac        300
ctaatggtgc agatcaatca gaagctggac gaagctatcc cggttcagtt tcctccgcag        360
atatatgaag ctatgaggta ttcagtcctt gccaaggtg ccaagcgagc cccacctgtt         420
atgtgcatct ctgcctgtga actctttggt ggcagccgcc ttgccgcctt tcccactgcc        480
tgtgcccttg aaatggttca tgcagcttca ttgatacacg atgatcttcc ctgcatggat        540
gactccccct cacgccgtgg tcagccttca aaccatacca tctatggtgt tgacatggca        600
attcttgcgg gcgatgcact ctttcccctt ggatttcgac acattgtttc acaaactcca        660
tcagaccttg tgcctgagtc gcacctcctt cgtgtgattg ccgagatagc ccgctctgta        720
ggatccactg gaatggctgc agggcagttc ctggaccttg aaggaggacc caatgcagtt        780
ggatttatac aagaaaaaaa gtttggtgaa atgggggagt cttctgcagt gtgtggagga        840
ttcttggctg gagctgaaga tgatgagata gagagactga ggaggtatgg gagagctgtt        900
ggggtattgt atgcagttgt ggatgatatt atagaagaga gattgaaagt tgagggagat        960
ggtgacagga aaacaagggg taagagttat gcagaggttt atggagttga aaaggcaata       1020 gaaaagctg aagagctcag agcaaaggct aagaagaat tggatggatt tgagaagcat        1080
ggggaacggg tctttcctct ctacagtttt gtggattatg cttttgatag aagtttcagt       1140
gttgatgatg ccagtggata a                                                1161
```

```
<210> SEQ ID NO 38
<211> LENGTH: 342
<212> TYPE: PRT
<213> ORGANISM: Glycine max

<400> SEQUENCE: 38

Met Ala Pro Phe Ala Phe Ala Thr Leu Pro Ser Ser His Ile Cys Arg
  1               5                  10                  15

Leu Pro Lys Pro Thr Asn Leu Lys Phe Arg Val Arg Cys Ser Thr Ala
             20                  25                  30

Ala Ser Ser Pro Ser Ser Val Ser Thr Arg Ser Lys Ala Ala Gly Phe
         35                  40                  45

Asp Leu Lys Thr Tyr Trp Ala Asn Leu Met Val Gln Ile Asn Gln Lys
     50                  55                  60

Leu Asp Glu Ala Ile Pro Val Gln Phe Pro Gln Ile Tyr Glu Ala
 65                  70                  75                  80

Met Arg Tyr Ser Val Leu Ala Lys Gly Ala Lys Arg Ala Pro Pro Val
                 85                  90                  95

Met Cys Ile Ser Ala Cys Glu Leu Phe Gly Gly Ser Arg Leu Ala Ala
            100                 105                 110

Phe Pro Thr Ala Cys Ala Leu Glu Met Val His Ala Ala Ser Leu Ile
        115                 120                 125

His Asp Asp Leu Pro Cys Met Asp Asp Ser Pro Ser Arg Arg Gly Gln
    130                 135                 140

Pro Ser Asn His Thr Ile Tyr Gly Val Asp Met Ala Ile Leu Ala Gly
145                 150                 155                 160

Asp Ala Leu Phe Pro Leu Gly Phe Arg His Ile Val Ser Gln Thr Pro
                165                 170                 175

Ser Asp Leu Val Pro Glu Ser His Leu Leu Arg Val Ile Ala Glu Ile
            180                 185                 190
```

-continued

```
Ala Arg Ser Val Gly Ser Thr Gly Met Ala Ala Gly Gln Phe Leu Asp
        195                 200                 205

Leu Glu Gly Gly Pro Asn Ala Val Gly Phe Ile Gln Glu Lys Lys Phe
    210                 215                 220

Gly Glu Met Gly Glu Ser Ser Ala Val Cys Gly Gly Phe Leu Ala Gly
225                 230                 235                 240

Ala Glu Asp Asp Glu Ile Glu Arg Leu Arg Arg Tyr Gly Arg Ala Val
                245                 250                 255

Gly Val Leu Tyr Ala Val Val Asp Asp Ile Ile Glu Glu Arg Leu Lys
            260                 265                 270

Val Glu Gly Asp Gly Asp Arg Lys Asn Lys Gly Lys Ser Tyr Ala Glu
        275                 280                 285

Val Tyr Gly Val Glu Lys Ala Ile Glu Lys Ala Glu Glu Leu Arg Ala
    290                 295                 300

Lys Ala Lys Glu Glu Leu Asp Gly Phe Glu Lys His Gly Glu Arg Val
305                 310                 315                 320

Phe Pro Leu Tyr Ser Phe Val Asp Tyr Ala Phe Asp Arg Ser Phe Ser
                325                 330                 335

Val Asp Asp Ala Ser Gly
            340
```

```
<210> SEQ ID NO 39
<211> LENGTH: 456
<212> TYPE: DNA
<213> ORGANISM: Triticum aestivum
<220> FEATURE:
<221> NAME/KEY: unsure
<222> LOCATION: (322)
<221> NAME/KEY: unsure
<222> LOCATION: (340)
<221> NAME/KEY: unsure
<222> LOCATION: (342)
<221> NAME/KEY: unsure
<222> LOCATION: (373)
<221> NAME/KEY: unsure
<222> LOCATION: (379)
<221> NAME/KEY: unsure
<222> LOCATION: (383)
<221> NAME/KEY: unsure
<222> LOCATION: (390)
<221> NAME/KEY: unsure
<222> LOCATION: (402)
<221> NAME/KEY: unsure
<222> LOCATION: (408)
<221> NAME/KEY: unsure
<222> LOCATION: (414)
<221> NAME/KEY: unsure
<222> LOCATION: (435)
<221> NAME/KEY: unsure
<222> LOCATION: (440)

<400> SEQUENCE: 39
cctagccggg tcagcctacc aacccaagaa accacatccg aacccaaatc tgcgcccctc      60
cgtcgccatg gctctctcat ccctcttcgt ctccctcccc ctccccatcc cgaagccgcc     120
atccacctcc aaatcaagcc gcttcctccc tatccgggcc tctgccgccg ccgcgaccgc     180
ctccccatct tttgacctgc gccgctactg gacctcgctg atctcggagg tcgacggcga     240
gctcgatgcc gcgatgccca tccgcccgcc ggagagcatc cacaacgcca tgcgccacgc     300
cgtcctcccg ggcgccggga angagggcgc cgccaagcgn gngcccccgg ttctctgcgt     360
cgccgcctgc gangctccnc ggngcgccgg cgccgcgggn gntcccancg acgncggcgc     420
tgggagatgc tcaangcggn tccctcgtgc acgaac                                456
```

```
<210> SEQ ID NO 40
<211> LENGTH: 102
<212> TYPE: PRT
<213> ORGANISM: Triticum aestivum
<220> FEATURE:
<221> NAME/KEY: UNSURE
<222> LOCATION: (86)
<221> NAME/KEY: UNSURE
<222> LOCATION: (93)

<400> SEQUENCE: 40

Ala Met Ala Leu Ser Ser Leu Phe Val Ser Leu Pro Leu Pro Ile Pro
 1               5                  10                  15

Lys Pro Pro Ser Thr Ser Lys Ser Ser Arg Phe Leu Pro Ile Arg Ala
            20                  25                  30

Ser Ala Ala Ala Thr Ala Ser Pro Ser Phe Asp Leu Arg Arg Tyr
        35                  40                  45

Trp Thr Ser Leu Ile Ser Glu Val Asp Gly Glu Leu Asp Ala Ala Met
    50                  55                  60

Pro Ile Arg Pro Pro Glu Ser Ile His Asn Ala Met Arg His Ala Val
65                  70                  75                  80

Leu Pro Gly Ala Gly Xaa Glu Gly Ala Ala Lys Arg Xaa Pro Pro Val
                85                  90                  95

Leu Cys Val Ala Ala Cys
            100

<210> SEQ ID NO 41
<211> LENGTH: 308
<212> TYPE: DNA
<213> ORGANISM: Triticum aestivum
<220> FEATURE:
<221> NAME/KEY: unsure
<222> LOCATION: (210)
<221> NAME/KEY: unsure
<222> LOCATION: (241)
<221> NAME/KEY: unsure
<222> LOCATION: (268)
<221> NAME/KEY: unsure
<222> LOCATION: (274)
<221> NAME/KEY: unsure
<222> LOCATION: (295)

<400> SEQUENCE: 41
cgacgacttg ccgtgctttg acgccgcgcc cacccgccga ggtcgcccgt ccacccacgc    60
ggcgtacggc acggacatgg ccgtcctcgc aggagacgcg ctcttcccgc tcgcctacac   120
ccacgtcatc tcccgcaccc cctcccccga ccccgtgtcg cacgccgtcc tcctccgcgt   180
tctcgcagaa ctcgcgcgca cgtggggatn caccggcatg gccgccggca ttcctccgat   240
ntcgccggtg ccaagcgcct cggtgaancc cgangtcatg caagtccttg acaangaatt   300
tcggcaaa                                                            308

<210> SEQ ID NO 42
<211> LENGTH: 76
<212> TYPE: PRT
<213> ORGANISM: Triticum aestivum
<220> FEATURE:
<221> NAME/KEY: UNSURE
<222> LOCATION: (48)
<221> NAME/KEY: UNSURE
<222> LOCATION: (70)

<400> SEQUENCE: 42

Asp Asp Leu Pro Cys Phe Asp Ala Ala Pro Thr Arg Arg Gly Arg Pro
```

```
                1               5              10              15

Ser Thr His Ala Ala Tyr Gly Thr Asp Met Ala Val Leu Ala Gly Asp
               20              25              30

Ala Leu Phe Pro Leu Ala Tyr Thr His Val Ile Ser Arg Thr Pro Xaa
               35              40              45

Pro Asp Pro Val Ser His Ala Val Leu Leu Arg Val Leu Ala Glu Leu
               50              55              60

Ala Arg Thr Trp Gly Xaa Thr Gly Met Ala Ala Gly
 65              70              75

<210> SEQ ID NO 43
<211> LENGTH: 1306
<212> TYPE: DNA
<213> ORGANISM: Triticum aestivum

<400> SEQUENCE: 43
gcacgagcct agccgggtca gcctaccaac ccaagaaacc acatccgaac ccaaatctgc      60
gccctccgt  cgccatggct ctctcatccc tcttcgtctc cctcccctc  ccatcccga     120
agccgccatc cacctccaaa tcaagccgct tcctccctat ccgggcctct gccgccgccg    180
cgaccgcctc cccatctttt gacctgcgcc gctactggac ctcgctgatc tcggaggtcg    240
agggcgagct cgatgccgcg atgcccatcc gcccgccgga gagcatccac aacgccatgc    300
gccacgccgt cctcccgggc gccgggaagg agggcgccgc caagcgcgcg ccccggttc     360
tctgcgtcgc cgcctgcgag ctcctcggcg cgccgcgcgc cgcggcgctc ccaccgccg    420
ccgcgctgga gatgctccac gcggcgtccc tcgtgcacga cgacctgccg tgcttcgacg    480
ccgcgcccac ccgccgaggt cgcccgtcca cccacgcggc ctacggcacg acatggccg    540
tcctcgcagg agacgcgctc ttccgctcg  cctacaccca cgtcatctcc cgcaccccct    600
ccccgaccc  cgtgtcgcac gccgtcctcc tccgcgttct cgcggaactc gcgcgcactg    660
tgggatccac cggcatggcc gccggccagt tcctcgacct cgccggtgcc agcgccctcg    720
gtgaagccga ggtcatgcag gtcctgacca agaagttcgg cgagatggcg gagtgctctg    780
ccgcgtgcgg ggctatgcta ggcggcgcgg gcccgacga  ggaggccgcg ttgcggcgat    840
acggccgcac catcggcgtc ctgtacgagc tcgtcgacga catgcggagc gcgtcgggaa    900
acggcaagat gaggagcaac gccagcgtcc tgcgctctct gggcatggac cgtgcgctgg    960
gcatcgtcga ggagctcaag gcgcaggcca agacggaggc ggacaggttc ggtgataagt   1020
atggcgaccg ggtgctgcct ctgtacagct tcgtggacta cgccgtggag aggggctttg   1080
agctccagga tgcagccacc gcgaagcttt aagcattggc acaggtgaca tgtagagtta   1140
tgtggtgctg aaattctgtc atctgaaact ctaaatttgt actatatgtg tttagaacat   1200
tagatgcgtg gttgctgttt ctgtccaaaa cttagcaagt ccctgaaata acatggtatc   1260
aaatgataaa cttatttgat aaaaaaaaaa aaaaaaaaa aaaaa                    1306

<210> SEQ ID NO 44
<211> LENGTH: 345
<212> TYPE: PRT
<213> ORGANISM: Triticum aestivum

<400> SEQUENCE: 44

Met Ala Leu Ser Ser Leu Phe Val Ser Leu Pro Leu Pro Ile Pro Lys
 1               5              10              15

Pro Pro Ser Thr Ser Lys Ser Ser Arg Phe Leu Pro Ile Arg Ala Ser
               20              25              30
```

```
Ala Ala Ala Thr Ala Ser Pro Ser Phe Asp Leu Arg Arg Tyr Trp
        35                  40                  45

Thr Ser Leu Ile Ser Glu Val Glu Gly Glu Leu Asp Ala Ala Met Pro
 50                  55                  60

Ile Arg Pro Pro Glu Ser Ile His Asn Ala Met Arg His Ala Val Leu
 65                  70                  75                  80

Pro Gly Ala Gly Lys Glu Gly Ala Ala Lys Arg Ala Pro Val Leu
                85                  90                  95

Cys Val Ala Ala Cys Glu Leu Leu Gly Ala Pro Arg Ala Ala Leu
                100                 105                 110

Pro Thr Ala Ala Ala Leu Glu Met Leu His Ala Ala Ser Leu Val His
            115                 120                 125

Asp Asp Leu Pro Cys Phe Asp Ala Ala Pro Thr Arg Arg Gly Arg Pro
130                 135                 140

Ser Thr His Ala Ala Tyr Gly Thr Asp Met Ala Val Leu Ala Gly Asp
145                 150                 155                 160

Ala Leu Phe Pro Leu Ala Tyr Thr His Val Ile Ser Arg Thr Pro Ser
                165                 170                 175

Pro Asp Pro Val Ser His Ala Val Leu Leu Arg Val Leu Ala Glu Leu
                180                 185                 190

Ala Arg Thr Val Gly Ser Thr Gly Met Ala Ala Gly Gln Phe Leu Asp
                195                 200                 205

Leu Ala Gly Ala Ser Ala Leu Gly Glu Ala Glu Val Met Gln Val Leu
210                 215                 220

Thr Lys Lys Phe Gly Glu Met Ala Glu Cys Ser Ala Ala Cys Gly Ala
225                 230                 235                 240

Met Leu Gly Gly Ala Gly Pro Asp Glu Glu Ala Ala Leu Arg Arg Tyr
                245                 250                 255

Gly Arg Thr Ile Gly Val Leu Tyr Glu Leu Val Asp Asp Met Arg Ser
                260                 265                 270

Ala Ser Gly Asn Gly Lys Met Arg Ser Asn Ala Ser Val Leu Arg Ser
                275                 280                 285

Leu Gly Met Asp Arg Ala Leu Gly Ile Val Glu Glu Leu Lys Ala Gln
                290                 295                 300

Ala Lys Thr Glu Ala Asp Arg Phe Gly Asp Lys Tyr Gly Asp Arg Val
305                 310                 315                 320

Leu Pro Leu Tyr Ser Phe Val Asp Tyr Ala Val Glu Arg Gly Phe Glu
                325                 330                 335

Leu Gln Asp Ala Ala Thr Ala Lys Leu
                340                 345

<210> SEQ ID NO 45
<211> LENGTH: 316
<212> TYPE: PRT
<213> ORGANISM: Lupinus albus

<400> SEQUENCE: 45

Met Leu Thr Lys Glu Asp Thr Val Lys Asp Lys Glu Glu Glu Glu
 1               5                  10                  15

Glu Glu Glu Lys Pro Arg Phe Asn Phe Asn Leu Tyr Met Val Glu Lys
                20                  25                  30

Ser Arg Ser Val Asn Gln Ala Leu Asn Asp Ala Val Ser Leu Arg Glu
            35                  40                  45

Pro His Lys Ile His Glu Ala Met Arg Tyr Ser Leu Leu Ala Gly Gly
```

```
                    50                  55                  60
Lys Arg Val Arg Pro Val Leu Cys Ile Ala Ala Cys Glu Val Val Gly
 65                  70                  75                  80

Gly Asn Glu Ser Thr Ala Met Ala Ala Ala Cys Ser Ile Glu Met Ile
                 85                  90                  95

His Thr Met Ser Leu Ile His Asp Asp Leu Pro Cys Met Asp Asn Asp
                100                 105                 110

Asp Leu Arg Arg Gly Lys Pro Thr Asn His Lys Val Phe Gly Glu Asn
                115                 120                 125

Ile Ala Val Leu Ala Gly Asp Ala Leu Leu Ala Phe Ala Phe Glu His
130                 135                 140

Ile Ala Val Ser Thr Ser Gly Val Ser Pro Glu Arg Ile Ile Gly Ala
145                 150                 155                 160

Ile Gly Glu Leu Ala Lys Ser Ile Gly Thr Glu Gly Leu Val Ala Gly
                165                 170                 175

Gln Val Val Asp Ile Asn Ser Glu Gly Leu Cys Asp Ile Gly Leu Glu
                180                 185                 190

Lys Leu Glu Phe Ile His Leu His Lys Thr Ala Ala Leu Leu Glu Gly
                195                 200                 205

Ser Val Val Gly Ala Ile Leu Gly Gly Cys Asn Glu Glu Val
210                 215                 220

Glu Lys Leu Arg Met Phe Ala Arg Tyr Ile Gly Leu Met Phe Gln Val
225                 230                 235                 240

Val Asp Asp Val Leu Asp Val Thr Lys Ser Ser Lys Glu Leu Gly Lys
                245                 250                 255

Thr Ala Gly Lys Asp Leu Val Ala Asp Lys Val Thr Tyr Pro Lys Leu
                260                 265                 270

Leu Gly Ile Glu Lys Ser Asn Glu Phe Ala Gln Lys Leu Asn Arg Asp
                275                 280                 285

Ala Gln Glu Gln Leu Ser Gly Phe Asp Pro Val Lys Val Ala Pro Leu
                290                 295                 300

Ile Ala Leu Ala Asn Tyr Ile Ala Tyr Ser Pro Asn
305                 310                 315

<210> SEQ ID NO 46
<211> LENGTH: 326
<212> TYPE: PRT
<213> ORGANISM: Arabidopsis thaliana

<400> SEQUENCE: 46

Met Leu Phe Ser Gly Ser Ala Ile Pro Leu Ser Ser Phe Cys Ser Leu
  1               5                  10                  15

Pro Glu Lys Pro His Thr Leu Pro Met Lys Leu Ser Pro Ala Ala Ile
                 20                  25                  30

Arg Ser Ser Ser Ser Ala Pro Gly Ser Leu Asn Phe Asp Leu Arg
             35                  40                  45

Thr Tyr Trp Thr Thr Leu Ile Thr Glu Ile Asn Gln Lys Leu Asp Glu
 50                  55                  60

Ala Ile Pro Val Lys His Pro Ala Gly Ile Tyr Glu Ala Met Arg Tyr
 65                  70                  75                  80

Ser Val Leu Ala Gln Gly Ala Lys Arg Ala Pro Pro Val Met Cys Val
                 85                  90                  95

Ala Ala Cys Glu Leu Phe Gly Gly Asp Arg Leu Ala Ala Phe Pro Thr
                100                 105                 110
```

-continued

```
Ala Cys Ala Leu Glu Met Val His Ala Ala Ser Leu Ile His Asp Asp
        115                 120                 125

Leu Pro Cys Met Asp Asp Pro Val Arg Arg Gly Lys Pro Ser Asn
        130             135                 140

His Thr Val Tyr Gly Ser Gly Met Ala Ile Leu Ala Gly Asp Ala Leu
145                 150                 155                 160

Phe Pro Leu Ala Phe Gln His Ile Val Ser His Thr Pro Pro Asp Leu
                165                 170                 175

Val Pro Arg Ala Thr Ile Leu Arg Leu Ile Thr Glu Ile Ala Arg Thr
            180                 185                 190

Val Gly Ser Thr Gly Met Ala Ala Gly Gln Tyr Val Asp Leu Glu Gly
        195                 200                 205

Gly Pro Phe Pro Leu Ser Phe Val Gln Glu Lys Lys Phe Gly Ala Met
        210                 215                 220

Gly Glu Cys Ser Ala Val Cys Gly Gly Leu Leu Gly Gly Ala Thr Glu
225                 230                 235                 240

Asp Glu Leu Gln Ser Leu Arg Arg Tyr Gly Arg Ala Val Gly Met Leu
                245                 250                 255

Tyr Gln Val Val Asp Asp Ile Thr Glu Asp Lys Lys Lys Ser Tyr Asp
            260                 265                 270

Gly Gly Ala Glu Lys Gly Met Met Glu Met Ala Glu Glu Leu Lys Glu
        275                 280                 285

Lys Ala Lys Lys Glu Leu Gln Val Phe Asp Asn Lys Tyr Gly Gly Gly
        290             295                 300

Asp Thr Leu Val Pro Leu Tyr Thr Phe Val Asp Tyr Ala Ala His Arg
305                 310                 315                 320

His Phe Leu Leu Pro Leu
                325
```